(12) United States Patent
Ishikawa et al.

(10) Patent No.: US 6,423,056 B1
(45) Date of Patent: Jul. 23, 2002

(54) INJECTABLE THERMAL BALLS FOR TUMOR ABLATION

(75) Inventors: Akira Ishikawa, Royce City; Nabuo Takeda, Richardson; Suzanne I. Ahn, Dallas, all of TX (US); Samuel S. Ahn, Los Angeles, CA (US); Steven R. Hays, Dallas, TX (US); F. Andrew Gaffney, Nashville, TN (US)

(73) Assignee: Ball Semiconductor, Inc., Allen, TX (US)

( * ) Notice: Subject to any disclaimer, the term of this patent is extended or adjusted under 35 U.S.C. 154(b) by 0 days.

(21) Appl. No.: 09/475,819

(22) Filed: Dec. 30, 1999

Related U.S. Application Data
(60) Provisional application No. 60/114,401, filed on Dec. 31, 1998.

(51) Int. Cl.$^7$ ............................................. A61B 18/18
(52) U.S. Cl. ........................... 606/28; 600/12; 607/113
(58) Field of Search .................. 607/101–103, 607/105, 113; 606/27, 28, 31, 33, 34; 600/9–13

(56) References Cited

U.S. PATENT DOCUMENTS

| | | | |
|---|---|---|---|
| 4,679,561 A | 7/1987 | Doss ........................... | 128/422 |
| 4,719,919 A | 1/1988 | Marchosky et al. ........ | 128/401 |
| 5,197,466 A | * 3/1993 | Marchosky et al. ........ | 607/113 |
| 5,468,210 A | * 11/1995 | Matsai et al. ................. | 600/10 |
| 5,571,152 A | 11/1996 | Chen et al. .................... | 607/92 |
| 6,053,937 A | * 4/2000 | Edwards et al. ............. | 607/101 |
| 6,164,284 A | * 12/2000 | Schulman et al. ........... | 128/899 |
| 6,167,313 A | * 12/2000 | Gray et al. ................... | 607/101 |
| 6,241,725 B1 | * 6/2001 | Cosman ........................ | 606/91 |

FOREIGN PATENT DOCUMENTS

| | | | |
|---|---|---|---|
| EP | 0 420 177 A1 | 4/1991 | ............ A61B/5/00 |
| WO | WO 98/43700 | 10/1998 | .......... A61N/1/365 |

* cited by examiner

Primary Examiner—Linda C. M. Dvorak
Assistant Examiner—David M. Ruddy
(74) Attorney, Agent, or Firm—Howison, Thoma & Arnott, L.L.P.

(57) ABSTRACT

A method of tumor ablation using injectable thermal-sensing balls. A catheter system (115) is used to inject a slurry (134) of thermal-sensing balls (136) into a tumor (122) located in, for example, a liver (120). The catheter system (115) comprises a catheter (128) and a specialized syringe (129) consisting of a housing (130) and a plunger (132). The housing (130) includes a cylindrical chamber having the slurry (134) of thermal-sensing balls (136). The catheter (128) is inserted retrograde into the femoral artery and passed to the site of the tumor (122). The hepatic artery (124) branches into smaller vessels, one of which is a tumor artery (126) which feeds the tumor (122). The tip of the catheter (128) is placed in the tumor artery (126) guided by conventional fluoroscopy. The injected balls (136) then receive energy from an external control system (110). The system (110) comprises a control panel (114) as an operator interface for controlling the system (110) and reading data therefrom. A CPU (112) is used for control and monitor of the operation, and transmits power and signals to the injected balls (136) via a radiating antenna (118), which energy is converted into heat to increase the temperature of the tumor (122). The temperature of the balls (136) can then be read from one or more onboard temperature sensors, and displayed to the operator for accurate control of the tumor temperature.

17 Claims, 11 Drawing Sheets

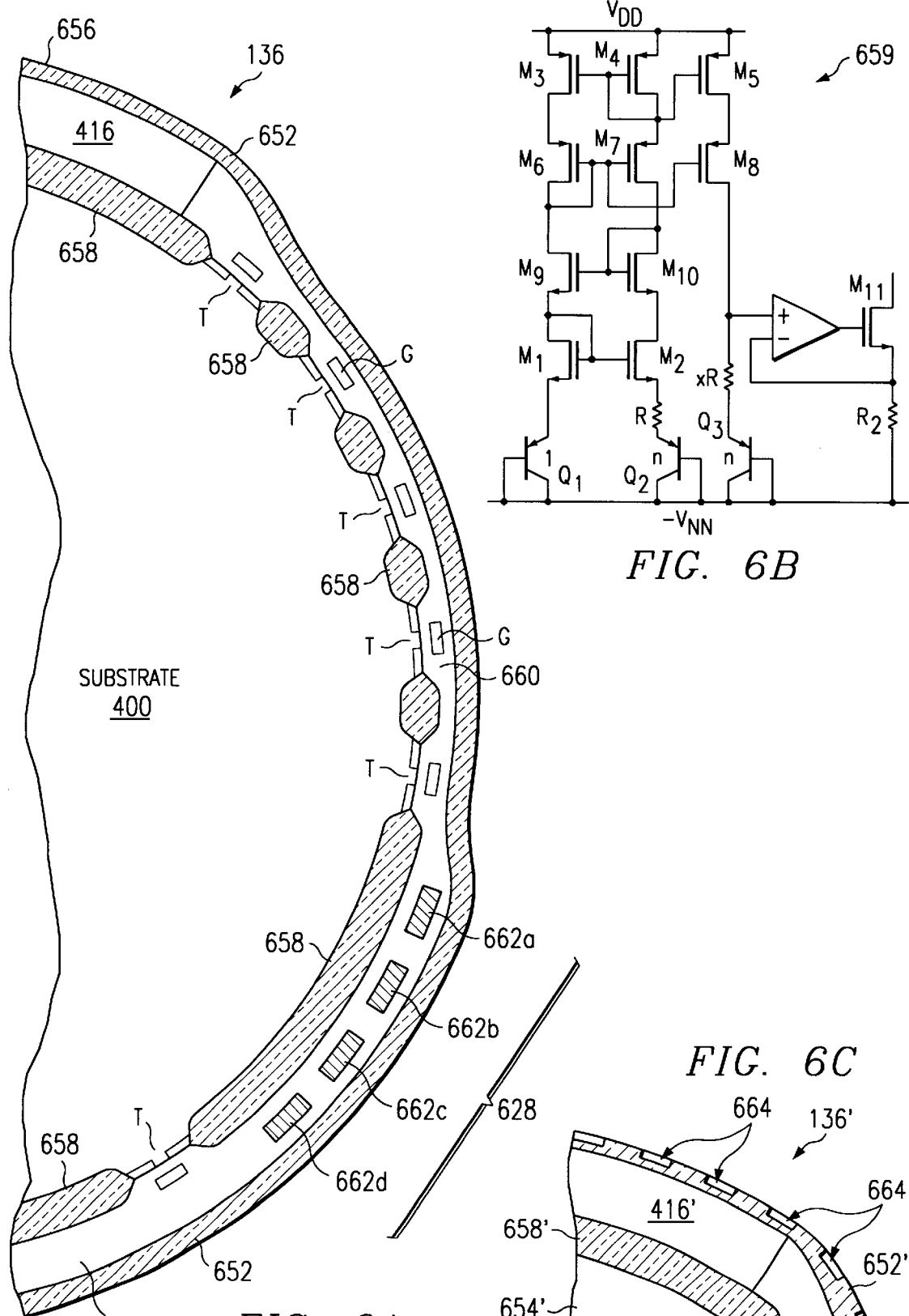
*FIG. 6B*
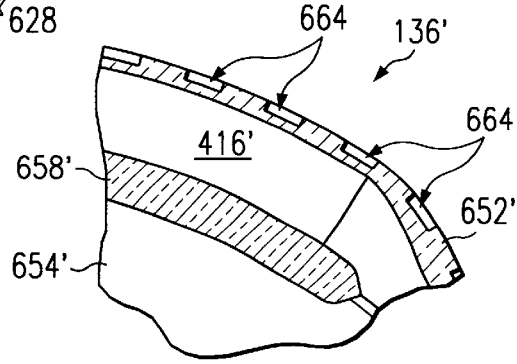
*FIG. 6C*
*FIG. 6A*

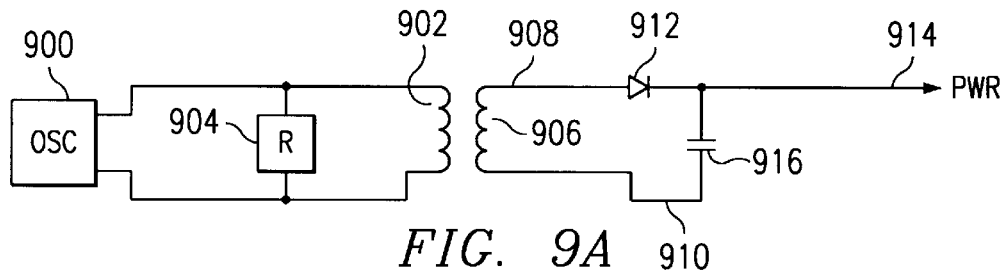
FIG. 9A
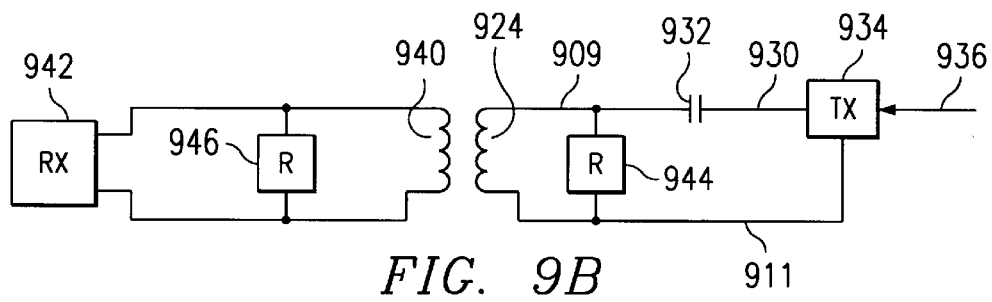
FIG. 9B
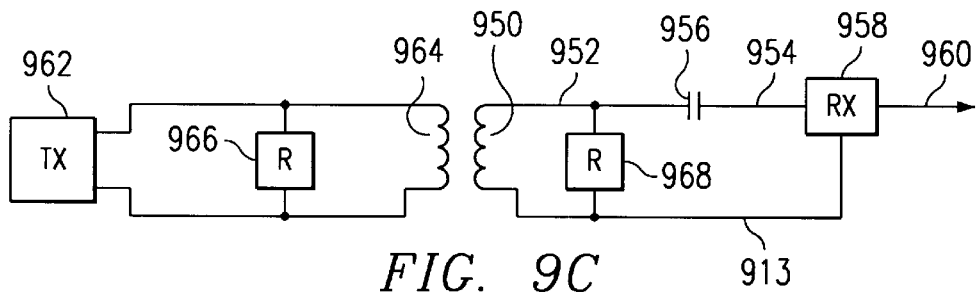
FIG. 9C
FIG. 10
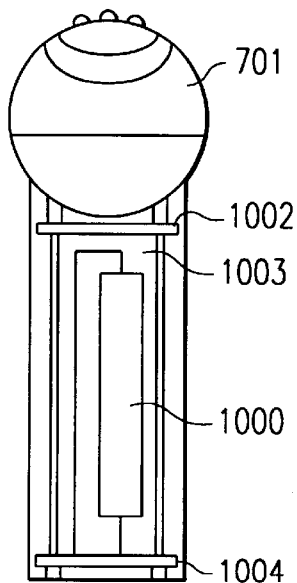
FIG. 11
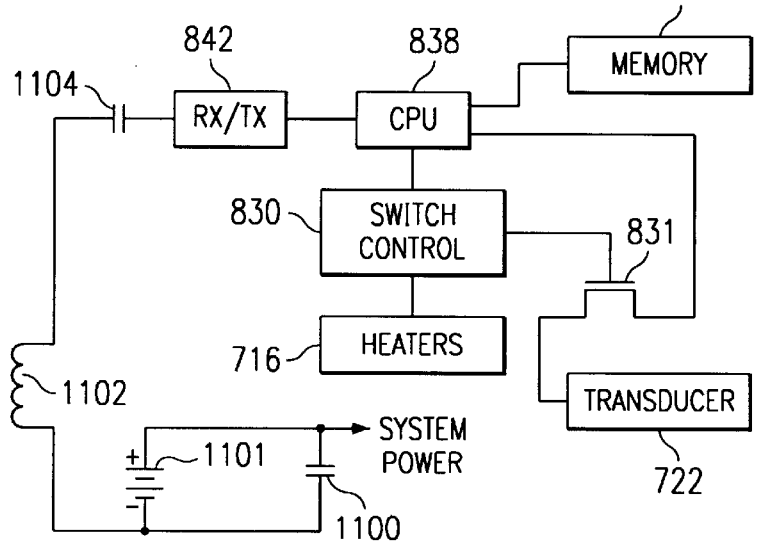

INJECTABLE THERMAL BALLS FOR TUMOR ABLATION

CROSS-REFERENCE TO RELATED APPLICATIONS

This application claims priority under 35 U.S.C. 119(e) from U.S. Provisional Patent Application Ser. No. 60/114,401 filed on Dec. 31, 1998, having the same title as this application.

This application is related to the following commonly assigned co-pending U.S. patent applications: Ser. No. 09/448,642 entitled "Miniature Spherical-Shaped Semiconductor With Transducer;" Ser. No. 09/448,641 entitled "Intraluminal Monitoring System;" Ser. No. 09/448,781 entitled "Spherical-Shaped Biomedical IC;" Ser. No. 09/448,678 entitled "Method of and System for Identifying Medical Products;" Ser. No. 09/448,638 entitled "Internal Thermometer;" and Ser. No. 09/448,644 entitled "Monitor for Interventional Procedures;" each of which were filed on Nov. 24, 1999, and each of which is incorporated herein by reference.

TECHNICAL FIELD OF THE INVENTION

This invention is related to devices and methods for treating tumors, and particularly to devices for localized heating of tumors.

BACKGROUND OF THE INVENTION

Currently, tumor ablation is commonly performed by external beam ionizing radiation or implantable ionizing radiation probes. However, these systems often deliver the energy in a relatively imprecise manner, leading to injury of surrounding healthy tissue. Furthermore, these systems involve ionizing radiation that can cause DNA mutation and potential for future cancer development.

Over the past 20 years radiant thermal energy has been used to provide thermal tumor ablation. These systems often involve the use of microwave or electromagnetic wave energy. The foremost problem in hyperthermia, however, is the generation and control of heat in the tumor's tissue. The effective temperature range of hyperthermia (42–45 degrees centigrade) is very small. At lower temperatures the affect is minimal; and at higher temperatures, normal cells are damaged. The response rate of tumor destruction is highly dependent on how much of the tumor is heated to a therapeutic level. Tumor temperatures are generally higher than the surrounding tissue during hyperthermia treatment because of the difference in tissue blood flow. The areas of most blood flow are heated less and tissues of less blood flow such as fat are heated more. Unfortunately, most tumors have a neovascularity which increases tissue blood flow and thus, makes the tumor less likely to heat relative to the surrounding fat. Accordingly, overheating of the surrounding fat remains a major problem, particularly in obese patients where the temperature rise may be seventeen times greater in fat than muscle due to the large difference in dielectric properties and specific heats.

Other problems particularly with inter-cavitary hyperthermia include temperature regulation. It is difficult to measure intratumor temperature by applying only external microwave or radio frequency energies. Temperatures have been measured on the surface of the tumor which may be very different from those in the tumor. Radio frequency energy can be deposited into the center of the body, but a large region is affected. Differential increases in blood flow in normal and tumor tissues may result in higher temperatures in the tumor than in normal organs. However, this temperature differential can not be ensured. Accordingly, large amounts of normal surrounding tissue may get injured during hyperthermia treatment.

More recently, various companies have developed a probe to be inserted directly into the tumor. This probe is capable of radiating thermal energy. However, most of the energy is limited to 2–5 millimeters surrounding the probe. Accordingly, uniform destruction of the tumor is difficult to obtain unless multiple probes are inserted into the tissue. Furthermore, the needles may often have to pass through normal vital tissue making needle-probe insertion hazardous or require an open surgery for insertion. More importantly, however, delivery of precise uniformly distributed energy to all the tumor cells is extremely difficult, if not virtually impossible, since the energy is concentrated at the center part of the temperature probe.

SUMMARY OF THE INVENTION

The present invention disclosed and claimed herein comprises, in one aspect thereof, a system for treating tumors. A processing unit is provided that is equipped with an antenna for transmitting and receiving signals, and including input control circuitry and display circuitry. One or more miniature substantially spherical heater balls are disposed proximate to the tumor. Each of the heater balls includes one or more heater elements and integrated circuitry for controlling the heater elements to radiate heat to the adjacent tumor. The integrated circuitry includes input/output data communication circuitry and signal processing circuitry for communicating with the processing unit to receive signals for the purpose of controlling the operation of the heater elements.

BRIEF DESCRIPTION OF THE DRAWINGS

For a more complete understanding of the present invention and the advantages thereof, reference is now made to the following description taken in conjunction with the accompanying Drawings in which:

FIG. 6 illustrates a more detailed semiconductor structure of the ball;

FIGS. 9A–C illustrate alternate embodiments for the transmit/receive operation;

FIG. 10 illustrates a side view of an alternative embodiment utilizing additional circuitry or structure attached to the ball for providing a local power source;

FIG. 11 illustrates a schematic block diagram of the ball using a battery as the local power supply system;

DETAILED DESCRIPTION OF THE INVENTION

Figure 1:
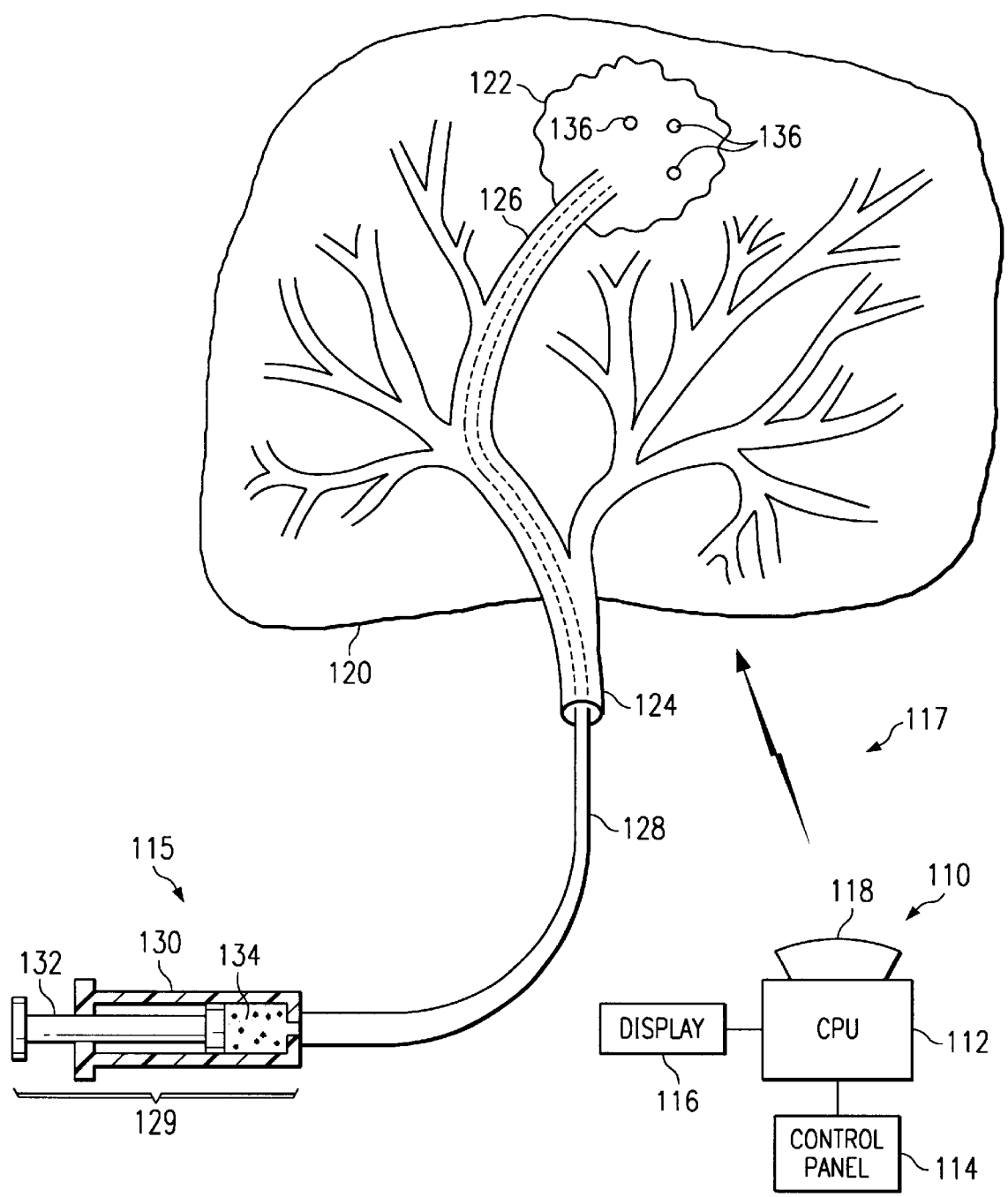
FIG. 1 illustrates a thermal ball system according to a disclosed embodiment.

Referring now to FIG. 1, there is illustrated a thermal ball system according to a disclosed embodiment. A thermal-sensing ball system 117 can be used for the treatment of tumor ablation in a patient. The system 117 includes a catheter system 115 and an external control system 110. The control system 110 comprises a central processing unit (CPU) 112, for monitor and control of the treatment, and an operator interface is provided in the form of a control panel 114 for use by a treating physician or medical practitioner to control the treatment by setting parameters such as the temperature set point and temperature duration of one or more thermal-sensing balls 136 deposited in a tumor 122 of, for example, a human liver 120. The CPU 112 outputs information regarding the status of the treatment on a system display 116. Communication with the implanted thermal-sensing balls 136 is by radio frequency (RF) transmission using a transmitting/receiving antenna 118. It will be appreciated that tumors 120 located elsewhere in the body can be similarly treated.

The liver 120 includes a complex system of arteries and arterioles which are fed by a patient's hepatic artery 124. A tumor artery or arteriole 126 feeds the tumor 122. The catheter delivery system 115 is used to inject the thermal-sensing balls 136 into the tumor 122. The catheter delivery system 115 includes a catheter 128 and a specialized syringe 129 consisting of a housing 130 and a plunger 132. The housing 130 (shown in cross-section) includes a cylindrical chamber having a slurry 134 of thermal-sensing balls 136. Forcing the plunger 132 into the housing 130 causes the slurry 134 to be injected into the catheter 128, and delivered to the tumor 122 through the catheter 128 which has been inserted into the tumor artery or arteriole 126. It will be appreciated that in many instances, it is preferable that the balls 136 are distributed uniformly throughout the tumor 122 such that the tumor ablation balls 136 will lodge within the arterioles within the tumor 122 blocking the infusion of fresh blood into the tumor 122 by the feeding vessels. The balls 136 then receive energy from the CPU 112 via the radiating antenna 118 and convert the energy into heat to increase the temperature of the tumor 122. In other instances, it may be desirable to provide localized heating of selected portions of the tumor 122. This scenario is desirable where the tumor 122 is sited in tissues which are less tolerant of heating as a method of tumor ablation, and can be accomplished by selectively disabling certain thermal-sensing balls 136 to obtain the localized heating effect, and which will be discussed in greater detail hereinbelow.

Access to the tumor 122 is provided through the femoral artery (not shown) endoluminally up into the hepatic artery 124 using conventional catheter insertion techniques. This conventional catheter-based technology allows a physician to deliver liquid or a slurry 134 to any part of the body through the feeding blood vessels. In the embodiment of FIG. 1, the catheter 128 is inserted retrograde into the femoral artery and passed into the aorta, the main artery of the body. The aorta branches to the celiac artery, which then branches to the hepatic artery 124 that feeds the liver 120. The hepatic artery 124 then branches into smaller vessels feeding different segments of the liver 120. One of the branches preferentially feeds the tumor 122, and the tip of the catheter 128 is placed in this tumor artery 126, guided by conventional fluoroscopy.

Figure 2:
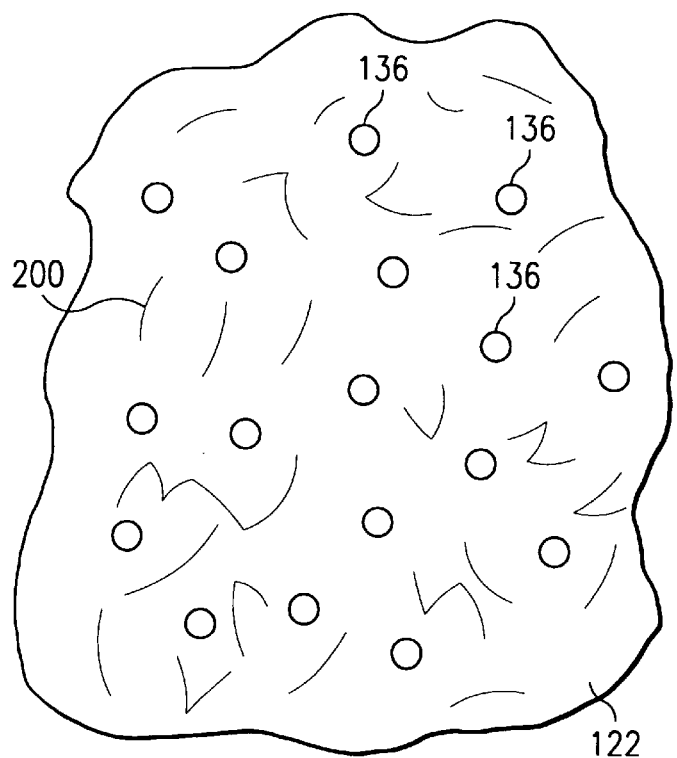
FIG. 2 illustrates an enlarged view of the tumor having the slurry of thermal balls inject thereinto.

Referring now to FIG. 2, there is illustrated an enlarged view of the tumor 122 having the slurry 134 of thermal balls 136 inject thereinto. With proper treatment, the thermal-sensing balls 136 are substantially uniformly distributed within the tumor 122, but do not extend into healthy tissue surrounding the tumor 122. The slurry 134 comprises a carrier liquid 200 having a benign impact on the living tissue. The carrier liquid 200 of the slurry 134 can also be selected to provide thermal properties which conduct more uniform heat transfer to the surrounding tumor tissues. On the other hand, other forms of treatment may include using a carrier liquid 200 which in and of itself is known to be effective in the treatment of tumors, but when heated properly, provides enhanced effectiveness of the treatment. Upon completion of the heating process, the slurry 134 comprising the carrier liquid 200 and the thermal-sensing balls 136 may be removed using the catheter system 115 which is already in place, or any other system capable of removing waste material from the treatment site.

Figure 3A:
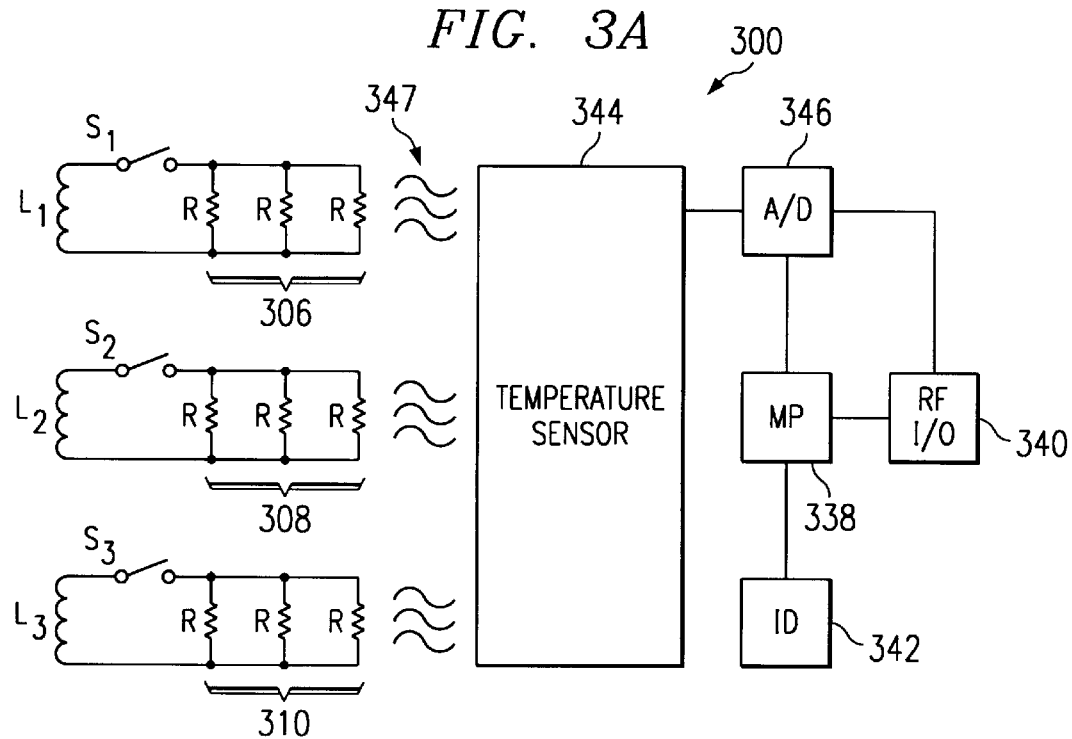
FIG. 3A illustrates a general circuit block diagram of the thermal-sensing ball.

Referring now to FIG. 3A, there is illustrated a general circuit block diagram 300 of the thermal-sensing ball 136. The circuit 300 includes a microprocessor (MP) 338 that controls all functions of the thermal-sensing ball 136. The circuitry of each thermal-sensing ball 136 is powered by an RF circuit which is part of an input/output (I/O) circuit 340. Each thermal-sensing ball 136 includes its own unique identification serial number (ID) stored in an ID memory 342. The heat generated on the ball 136 is measured by a temperature sensor 344, which provides analog temperature information to an analog-to-digital converter (A/D) 346. Alternatively, analog temperature data can be modulated onto an RF carrier frequency and transmitted by the I/O circuit 340. Since it is useful to transmit digital ID information from ID memory 342 along with the temperature data, it is preferable to convert the temperature data to digital form using the A/D converter 346. The structure of the temperature sensor 344 may be a circuit containing a large-area diode whose forward current is calibrated to measure temperatures in a narrow range. It is well known that a slightly forward-biased PN junction has a temperature-dependent forward current. As will be mentioned hereinbelow, the temperature-sensing operation may also be performed using a band gap reference circuit.

Thermal energy 347 is generated on the thermal-sensing ball 136 by way of coupling energy signals to receiving coils $L_1$, $L_2$ and $L_3$, each of which couples transmitted energy from the control system 110 into one or more sets (306, 308, and 310) of resistive heater elements R. The heater elements R can be implemented as resistive polycrystalline strips on the surface of each thermal-sensing ball 136, as will be discussed in greater detail hereinbelow. The coils $L_1$, $L_2$ and $L_3$ are preferably arranged in mutually orthogonal planes so that the thermal-sensing ball 136 receives RF energy regardless of its orientation in the tumor 122. Power to the heater elements R is switched by respective switches $S_1$, $S_2$ and $S_3$, of the coils $L_1$, $L_2$ and $L_3$. The switches $S_1$, $S_2$ and $S_3$ are implemented as transistors which are controlled by the microprocessor 338, and can be opened to selectively disable the resistive heating elements R. This feature allows heat generation to be remotely controlled by the control system 110 to more effectively treat the tumor 122.

Figure 3B:
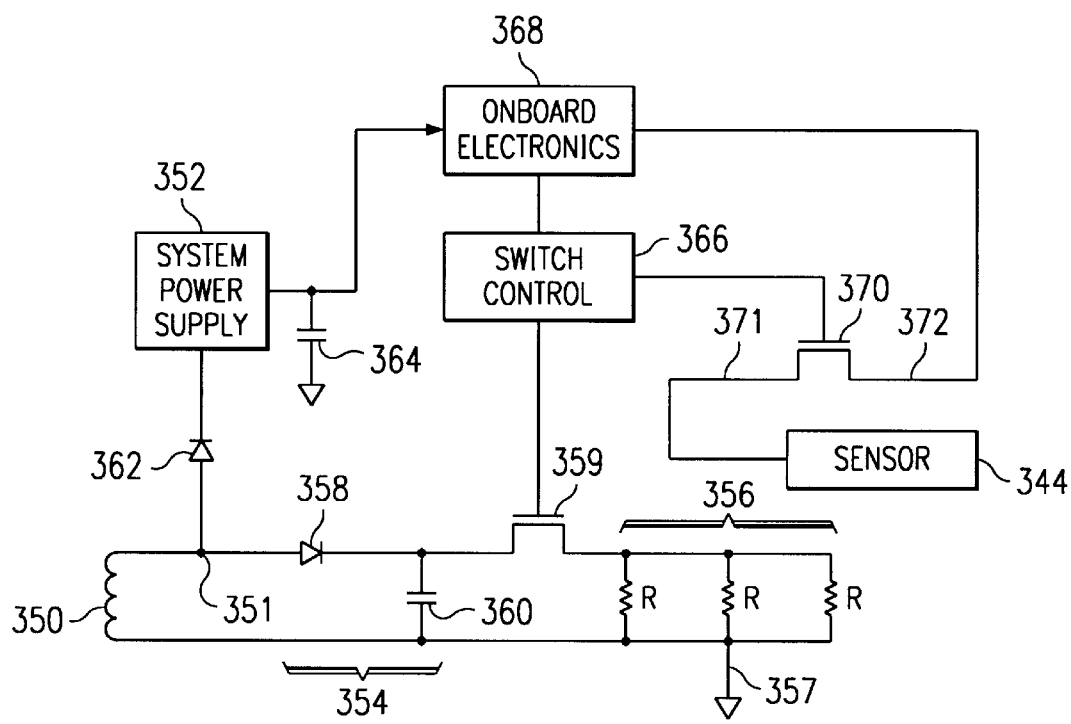
FIG. 3B illustrates a general circuit block diagram of the power supply structure for both the onboard circuits and the heater section.

Referring now to FIG. 3B, there is illustrated a general circuit block diagram of the power supply structure for both the onboard circuits and the heater section. It can be appreciated that independent power supplies are suggested, since implementation of a single power supply source for both the heaters and the onboard system electronics may cause a momentary voltage variation (or power spike) in the system power such that operation of the control electronics could be disrupted. Therefore, an onboard coupling element 350 (e.g., an inductor) is provided to power two power sources; a system power supply 352 for all onboard electronics, and a heater power supply 354 for a heater section 356. The control system 110 radiates energy through the radiating antenna 118 which is coupled into the coupling element 350.

Power for the heater section 356 passes through a blocking diode 358 and is stored in a capacitor 360. The anode of the diode 358 connects to a node 351. The cathode connects to the upper plate of the capacitor 360, and to one drain/source leg of a switching transistor 359. The other drain/source leg of the switching transistor 359 connects to the parallel resistances R of the heater section 356. The lower plate of the capacitor 360 connects to a ground potential node 357, which can be the substrate of the semiconductor thermal-sensing ball 136. The heater resistances R and the lower leg of the coupling element 350 also connect to this ground node 357. The gate of the heater switching transistor 359 connects to a switching control circuit 366 for operational control of the switching transistor 359 for ultimately enabling current to flow from the coupling element 350 and the heater capacitor 360 to the heater section 356. The voltage drop across the diode 358 is minimal, but any losses can contribute to the overall heating effect for tumor ablation. Thus, a Schlottky diode may be utilized for diode 358 with a lower forward drop. The capacity for the heater capacitor 360 may be realized by utilizing the lower hemisphere of the substantially spherical thermal-sensing ball 136 or even a separate ball.

Similarly, power to the system electronics passes through a blocking diode 362 to the system power supply 352. The anode of the diode 362 connects to the upper leg of the coupling element 350, which is the node 351. The cathode connects to the system power supply block 352. At the output of the system power supply block 352 is a power capacitor 364 which stores charge for operation of the onboard system electronics, and also provides a smoothing function for any power fluctuations that may occur. The output of the system power supply 352 connects to provide power to an onboard electronics block 368, which represents the processor 338, A/D 346, RF I/O 340, ID memory 342, and other circuits not illustrated. The onboard electronics functions to control the switch control circuit 366 according to stored instructions, or to instructions transmitted from the control system 110 to the one or more thermal-sensing balls 136. The onboard electronics 368 also function to control a sensing transistor 370 to read the output of the sensor 344 via the gate of the sensing transistor 370. One drain/source leg 371 of the sensing transistor connects to the sensor 344, while the other drain/source leg 372 connects back to the onboard electronics 368.

Figure 3C:
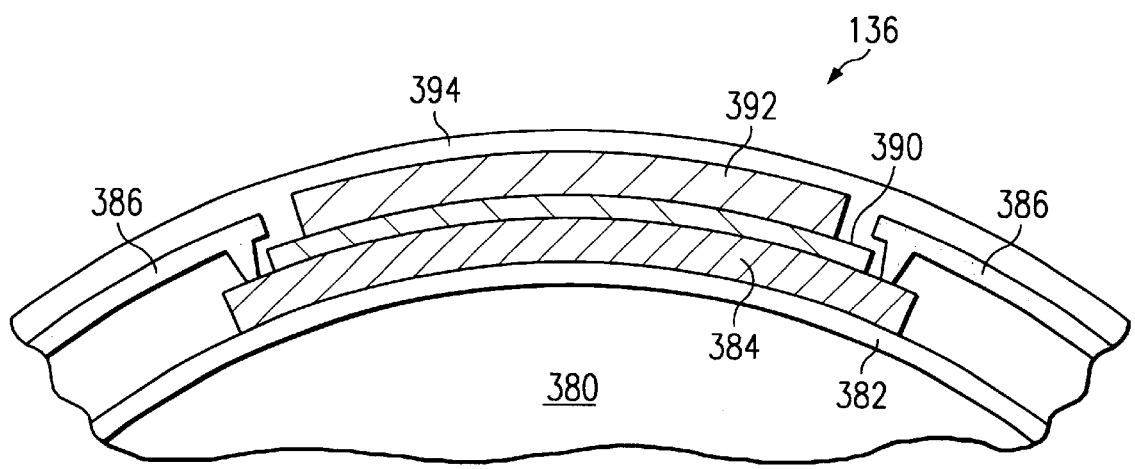
FIG. 3C illustrates a semiconductor heating device, according to a disclosed embodiment.

Referring now to FIG. 3C, there is illustrated a semiconductor heating device, according to a disclosed embodiment. The thermal-sensing ball 136 has associated therewith one or more sets of heating elements (306, 308, and 310) which are formed onto a substrate 380. A passivation layer 382 if formed over the substrate 380, and consists of $SiO_2$. Overlying the passivation layer 382 is a poly layer 384 of approximately 600 angstroms. The polycrystalline layer 384 is appropriately doped to provide the resistive properties for the desired thermal output. A metal layer is then deposited and etched to form metal contacts 386 at both ends of the poly layer 384. Current is conducted through the metal contacts 386 through the poly layer to provide the thermal effect. Another passivation layer 390 is formed over the poly/metal layers (384 and 386, respectively) to provide isolation from the underlying poly layer 384 and an overlying metal heat sink 392 then disposed on he surface of layer 390. The metal heat sink 392 can be made of an aluminum and copper alloy for ready thermal sinking of the underlying heat generated by the resistive poly layer 384. Finally, an overlying passivation layer 394 is provided to electrical isolate all circuitry on the thermal-sensing ball 136 from the contact medium.

Notably, it may be desirable to fabricate the heating elements (306, 308, and 310) on the surface of the ball 136 which is away from the onboard electronics (except the temperature sensor which measures the output of the thermal circuits) to provide a level of electrical stability to such circuits during the heating phase. This approach may be more conducive to a situation where the heating and temperature-sensing components are fabricated on a first ball, and the control electronics are fabricated on second ball which interfaces to the first ball for interfacing thereto. In this case, a third ball may be fabricated to provide an independent and stand-alone power source, independent from the transmitted power of the control system 110.

This scenario is discussed in greater detail hereinbelow.

It will be appreciated that as an additional feature of the disclosed architecture, an infrared image can be superimposed on a fluoroscopic map of the region of the body surrounding the tumor 122. A map of all of the thermal-sensing balls 136 and respective unique IDs (or addresses) stored in memory 342 can be obtained such that an individual thermal-sensing ball 136 can be selectively energized by addressing only those balls 136 in the vicinity of the zone which is desired to be heated. Accordingly, any thermal-sensing balls 136 that are misplaced outside the tumor 122 into healthy tissue can be visually identified and disabled to prevent thermal damage to surrounding healthy tissue. Additionally, by providing the capability of addressing individual thermal-sensing balls 136, the heating of the tumor 122 can be more effectively controlled to within a precise temperature range.

As an alternative to providing both heating and temperature sensing on each thermal-sensing ball 136, the heating and sensing functions can be separated such that distinct temperature sensing-only balls can be blended into the slurry 134 along with a larger number of thermal-only balls. For example, ten temperature sensing 20 only balls can be mixed with fifty thermal-only balls, all of which are injected into the tumor 122 and are substantially randomly distributed therein. This technique permits a more direct resultant measurement of the effectiveness of the heating of tumor 122 tissues as the heating process continues, whereas the consolidation of the heating and sensing functions on a single thermal-sensing ball 136 offers more control over the heating process, but less feedback on the resultant heating effects on the tumor 122 tissue itself. As mentioned hereinabove, each of the temperature sensing-only balls also can be made to be separately addressable according to a unique ID stored in an onboard non-volatile memory to obtain a distribution of temperatures in selected areas throughout the tumor 122.

The sensor and/or heater balls used in ablation of the tumor 122 will generally be approximately one millimeter in diameter, but can be larger or smaller depending upon the dimensional needs of the recipient blood vessel. The arterial system 126 that feeds the tumor 122 terminates in small arterioles that are approximately one millimeter in diameter or less. These arterioles then branch into microscopic capillaries. Therefore, tumor ablation balls 136 of approximately one millimeter in diameter could lodge into the arteriole, and stop at the pre-capillary level to choke off fresh blood circulation to the tumor 122. This eliminates the cooling effect to the tumor 122 provided by circulating blood in the tumor tissue. Temporary blocking of the vessels providing blood flow to the tumor 122 allows for more effective heating of the tumor tissue during treatment.

In alternative embodiments, the tumor ablation balls 136 can also be fabricated to include sensors that can detect pH, $O_2$, and $CO_2$ content to help the physician determine when all the tumor tissue has been destroyed, since dead tissue will have a different pH, $O_2$, and $CO_2$ content than normal healthy tissue. Additionally, the thermal balls 136 can also be used to ablate other non-cancerous tissues or organs such as abnormally enlarged spleen, uterine fibroid, and endometriosis. The disclosed architecture can also be used for various vascular tumors such as hemangiomas, spider talecgentasia, and arterial venousmal formations, to name a few.

Figure 4:
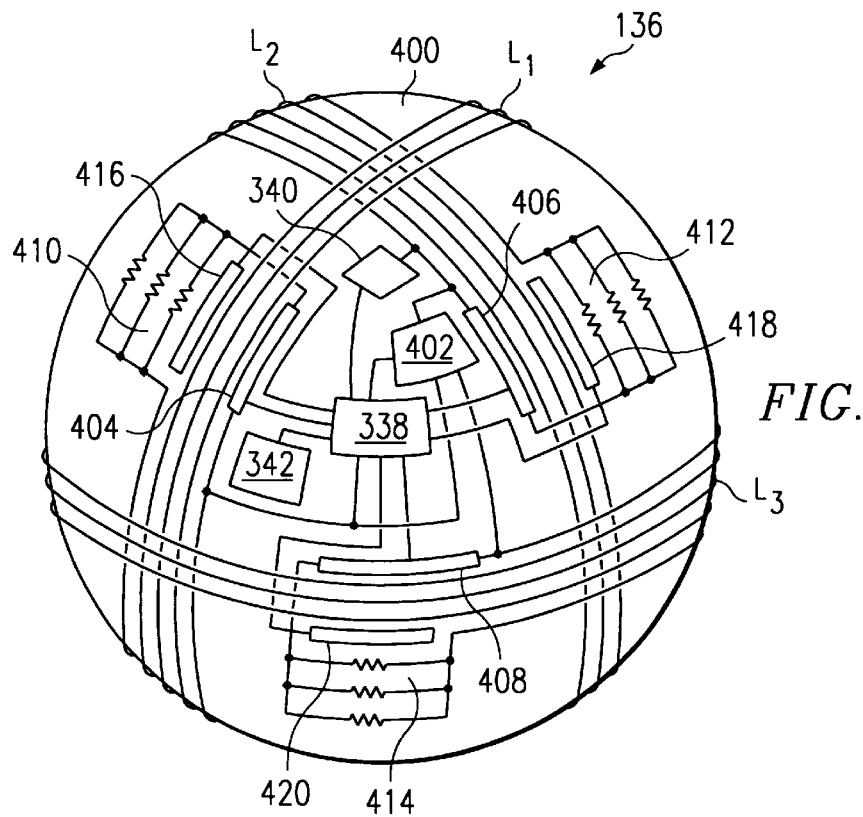
FIG. 4 illustrates a physical diagram of a thermal-sensing ball and associated exposed circuit blocks.

Referring now to FIG. 4, there is illustrated a physical diagram of a thermal-sensing ball 136 and associated exposed circuit blocks. The ball 136 comprises a substrate 400 upon which the numerous onboard circuit elements are fabricated. The coils $L_1$, $L_2$, and $L_3$ are oriented substantially orthogonally to one another for coupling energy and signals to the circuits of the ball 136 when in any orientation of the slurry 134 within the tumor 122, and transmitting signals therefrom. One end of each of the coils $L_1$, $L_2$, and $L_3$ is connected to a power regulator 402, and respective control switches 404, 406, and 408, which control switch is controlled by the microprocessor 338. The other end of each of the three coils $L_1$, $L_2$, and $L_3$ is connected to respective resistive ladders of heating elements 410, 412, and 414 (similar to resistive elements R). The microprocessor 338 provides monitor and control functions for all activities on the thermal-sensing ball 136. The microprocessor 338 is illustrated as comprising the A/D function of the A/D 346, which combined functions can be found in conventional digital signal processing (DSP) circuits. The microprocessor 338 connects to and controls the three switches 404, 406, and 408 for controlling the amount of energy coupled from each of the respective coils $L_1$, $L_2$ and $L_3$ to respective heating elements 410, 412, and 414. It can be appreciated that the microprocessor 338 can be programmed from the control system 110 to cycle power to each of the heating elements 410, 412, and 414 in a predetermined fashion. For example, energy switched in the form of current to heating element 410 may be cycled once every time period, while current switched to heating element 412 is switched ten times per the same time period, and current switched to heating element 414 is switched twenty-five times per the same time period. This flexibility offers more accurate and effective control of heat being applied by the thermal-sensing balls 136 to the tissues in and around the tumor 122.

The power regulation circuit 402 connects to each of the unswitched sides of the coils $L_1$, $L_2$ and $L_3$ to obtain the maximum power transmitted. For example, if the orientation of the ball 136 is such that the coupled power signal is the greatest on coil $L_3$, yet weaker on coils $L_1$, and $L_2$, the maximum power is still obtainable. Had the power regulator been connected to only a single coil, the amount of power coupled to the ball 136 would be problematic based upon the orientation of the coils in the electric field provided by the control system 110. As mentioned hereinabove, the power regulator 402 provides power to all onboard circuits during operation of the ball 136.

In close proximity to each set of heating elements 410, 412, and 414, respective temperature sensors 416, 418, and 420 are fabricated to accurately monitor the temperature of the respective heating elements. In this way, all or selected ones of the heating elements 410, 412, and 414 can be monitored to obtain more accurate control of the desired heating effect for tumor ablation. Each temperature sensor 416, 418, and 420 connects to the microprocessor 338 for power, A/D conversion, and processing of the measured data.

The RF transmit/receive circuit 340 connects to the microprocessor to provide I/O functions for RF signals coming into the ball 136 from the control system 110, and for the transmission of communication signals from the ball 136 to the control system 110. The RF circuit 340 is illustrated as having a single connection to coil/antenna $L_2$, when in practice it could be connected to any or all three coils $L_1$, $L_2$ and $L_3$ to ensure adequate reception and signal transmission strength to the control system 110. The RF transmit/receive circuit 340 can also obtain power through the connection from the microprocessor 340, or have its own dedicated connection (not shown) from the power regulator circuit 402. Note that the coils $L_1$, $L_2$ and $L_3$ are used for power coupling and signal communication between the ball 136 and the control system 110. Therefore, the communication signal may be modulated into the power signal to provide a more continuous exchange of power and signals. Additionally, the number of coil windings can be varied according to the required power levels.

The memory 342 connects to the microprocessor 338, is non-volatile, and stores the unique ID of the ball 136. The unique ID can be accessed upon command from the control system 110. It can be appreciated that the memory 342 can be programmed according to the user's needs. For example, in addition to the unique ID, the memory may contain information related to the patient, such as name, address, date of usage of the ball 136, the attending physician and hospital, circumstances under which the ball was used (tumor ablation of the liver), etc. Additionally, where a plurality of balls 136 are used, a group of the balls 136 may be programmed with a common ID such that during operation, a selected group of balls 136 in the slurry 134 may be energized, while others are not. This feature may be used where more than one slurry 134 is used, each slurry 134 delivering balls 136 for different functions. Note also that the unique ID can be programmed at the site by the control system 110 prior to introduction of the slurry 134 into the tumor 122.

Figure 5:
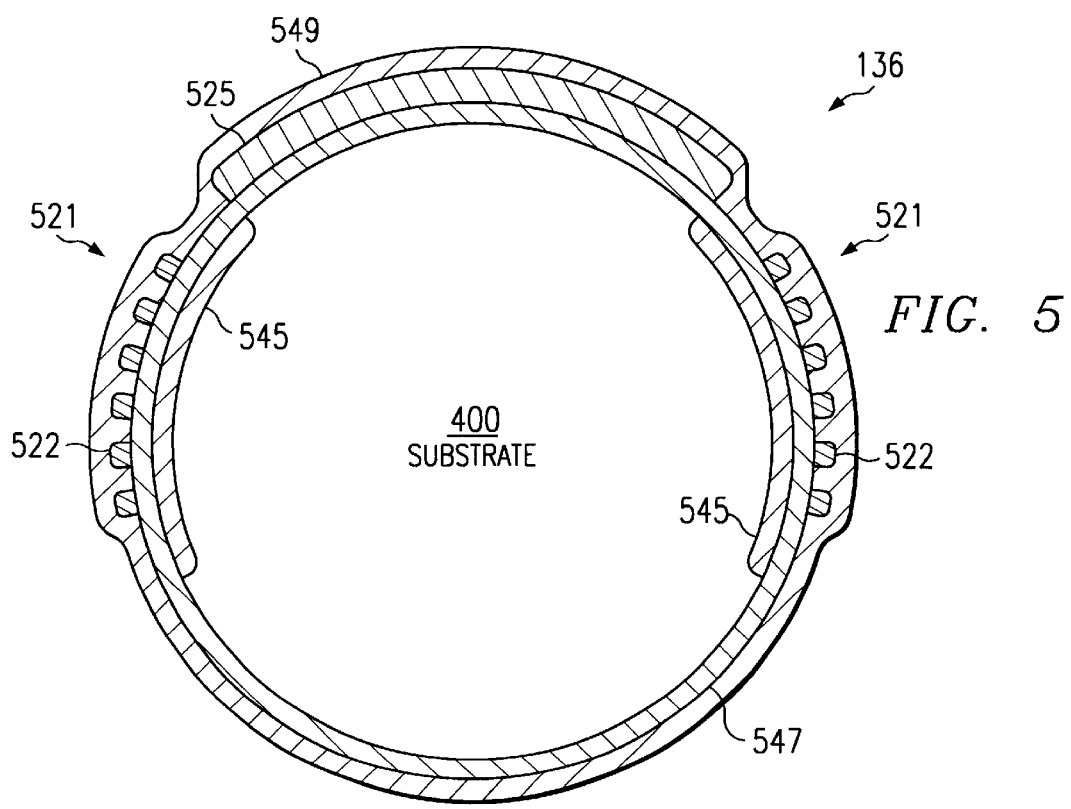
FIG. 5 illustrates a cross section of a thermal-sensing ball.

Referring now to FIG. 5, there is illustrated a cross section of a thermal-sensing ball. The ball 136 preferably comprises a spherical-shaped semiconductor device on which an integrated circuit has been formed. Such a spherical-shaped integrated circuit semiconductor device (commonly referred to herein as a "ball") is described in commonly assigned U.S. Pat. No. 5,955,776, filed May 16, 1997, issued Sep. 21, 1999, entitled "Spherical-Shaped Semiconductor Integrated Circuit," the disclosure of which is incorporated herein by reference. The ball 136 is built on a substantially spherical semiconductor substrate 400, which may be doped with P-type or N-type impurities in accordance with the particular requirements of the fabrication process. Semiconductor circuitry, indicated generally at 545, resides on substrate 400. Circuitry 545 includes the power regulator 340, an RF interface circuitry 340 with mixing circuit and amplifier, as well as other circuitry. Substrate 400 and circuitry 545 are covered by an insulating layer 547. Insulating layer 547 is preferably formed of silicon dioxide or phosphosilicate glass. A temperature sensor 525 is disposed on the surface of insulating layer 547. Suitable connections are provided through the insulating layer 547 to circuitry 545.

A power and transmit/receive coil 521 (only one shown, and similar to each coils $L_1$, $L_2$ and $L_3$) is formed of helically-wrapped windings over the insulating layer 547. The power coil 521 may have any number of individual windings 522 which can be fabricated from a deposited layer of aluminum that is patterned and etched using conventional semiconductor fabrication techniques. The actual number of individual windings of power coil 521 may be far greater than the six illustrated.

The ball 136 is coated with or encapsulated in a layer 549 of biologically inert material such as phosphosilicate glass. The coating 549 can withstand the acidity of the stomach to a pH level of about 1.5, and it is not subject to the enzymatic actions in the digestive tract, or other body chemicals to which it is subjected. The ball 136 is substantially spherical and preferably about one millimeter in diameter. The very small size and round shape facilitates use with the catheter system 115, and for implantation. However, the ball 136 should be made large enough to prevent absorption through structures in which the balls 136 are to be implanted, for example, if the balls 136 are to be used in the digestive tract, the microvilli in the lining of the digestive tract.

Referring now to FIG. 6A, there are illustrated semiconductor details of the ball 136. The ball 136 is hermetically protected by a thin exterior glass passivation layer 652, which may be phosphosilicate glass (PSG). The interior of the ball 136 comprises a semiconductor substrate 400, which may be doped p-type or n-type in accordance with the particular requirements of the fabrication process. Optionally, the substrate 400 may be connected to a stent or other metallic intraluminal device to serve as a ground potential for the ball 136. The temperature transducer 416 has an outer surface 656 that is exposed to the tumor tissue or slurry carrier liquid 200, when implanted in the tumor 122. The transducer 416 (and similarly for transducers 418 and 420) preferably is formed atop a thick dielectric layer 658, which may be a field oxide layer grown on the substrate 400. Note that more or less transducers and coils may be used to achieved the desired results.

A large number of transistors T make up the circuitry of the voltage regulator 340, microprocessor 338, and other onboard circuits described hereinabove. Although these transistors T are schematically depicted as MOS transistors, the integrated circuitry of the ball 136 could also use bipolar transistors. The individual transistors T are shown separated by portions of the field oxide 658. Transistor gates G and circuit interconnections (not shown) are embedded in an inter-level dielectric layer 660, and are made using conventional semiconductor fabrication techniques adapted to the spherical surface of the ball 136.

The antenna/power coil 521, described in connection with FIG. 5, is shown as having a plurality of separate windings 662a, 662b, 662c and 662d, which may be fabricated from a deposited layer of aluminum (or copper) that is patterned and etched using conventional semiconductor fabrication techniques adapted to the spherical shape of the ball 136. The windings (662a, 662b, 662c, and 662d) are insulated from each other by portions of the inter-level dielectric layer 660. The actual number of individual windings of the coil 522 may be far greater than the four specific windings shown. The ends of the coil 522 are connected by additional conductors (not shown) to other circuit elements of the ball 136.

Referring now to FIG. 6B, there is illustrated a schematic diagram of a temperature-compensated current source. The current source is comprised of two legs. The first leg has disposed between a positive and negative rail, four MOS transistors and a bipolar transistor. The first MOS transistor is a P-channel transistor labeled $M_3$ having a source/drain path connected between a positive rail and the source-drain path of a P-channel transistor $M_6$. The other side of the source/drain path of transistor $M_6$ is connected to the gate thereof, and also to the one side of the source/drain path of N-channel transistor $M_9$, the other side thereof connected to one side of the source/drain path of an N-channel transistor $M_1$, and also to the gate of transistor $M_6$. The other side of the source/drain path of transistor $M_1$, is connected to the emitter of a P-channel transistor $Q_1$. The base and collector of transistor $Q_1$ are connected to the ground terminal. The other leg of the current source has a P-channel transistor $M_4$ with one side of the source/drain path thereof connected to the positive rail, the other side thereof connected to one side of the source/drain path of a P-drain transistor $M_7$ and also to the gate of transistor $M_4$ and the gate of transistor $M_3$.

The other side of the source/drain path of transistor $M_7$ is connected to one side of the source/drain of N-channel transistor $M_{10}$ and also to the gate of transistor $M_7$ and the gate of transistor $M_6$, and also to the gate of transistor $M_{10}$. The other side of the source/drain path of transistor $M_{10}$ is connected to one side of the source/drain path of an N-channel transistor $M_2$, the gate thereof connected to the gate of transistor $M_1$ (the gate of transistor $M_{10}$ connected to the gate of transistor $M_9$ and the gate of transistor $M_7$ connected to the gate of transistor $M_6$). The gate of transistor $M_2$ is connected to the gate of transistor $M_1$. The other side of the source/drain path thereof is connected to one side of a resistor R. The other side of resistor R is connected to the emitter of a PNP transistor $Q_2$, the base and collector thereof connected to ground. The transistors $M_1$–$M_4$, $M_7$ and the bipolar transistors $Q_1$ and $Q_2$, form a conventional supply-independent circuit. The leg associated with transistor $Q_1$ provides the reference link with the current source, and the transistor's associated leg in bipolar transistor $Q_2$ provide the function of the mirror leg.

The current through transistor $M_4$ is utilized to generate a bias voltage on the gate of transistor $M_3$ to control a current therethrough. Therefore, the current through transistor $M_4$ is essentially reflected over to transistor $M_3$ such that the current through transistor $M_3$ is equal to the current through transistor $M_4$. The transistors $M_1$ and $M_2$ allow a voltage on the emitter of transistor $Q_1$ to be reflected over to the top of resistor R such that the voltage on the emitter of transistor $Q_1$ and the voltage on the top of resistor R are substantially equal. The current through resistor R generates a voltage $\Delta V_{BE}$ thereacross, which represents the difference in the base-emitter voltages of the two transistors $Q_1$ and $Q_2$. Although the current is equal through both base-emitter junctions of transistors $Q_1$ and $Q_2$, there is a small difference in the base-emitter voltage, this being the voltage developed across the resistor R, this being a Temperature Proportional to Absolute Temperature (TPAT). This current is subtracted from a temperature-stable current to therefore provide an offset current. This offset current is inversely proportional to temperature.

The gates of transistors $M_3$ and $M_6$ are output to two series-connected P-channel transistors $M_8$ and $M_5$, respectively, disposed between the positive supply and the positive input of a unit gain amplifier. This positive input is also connected to one side of a bias resistor, the other side of which is connected to the emitter of a PNP transistor $Q_3$, the base and collector thereof connected to ground. The output of the amplifier is connected to the gate of N-channel transistor $M_{11}$, the drain thereof connected to the negative input of the amplifier, and also to one side of an output load resistor $R_2$, connected on the other side thereof to ground. The source of transistor $M_{11}$ provides a voltage output, which constitutes a temperature-dependent voltage.

Referring now to FIG. 6C, there is illustrated a recessed portion 136' of the ball 136, using similar reference numerals which designate similar elements. The recessed portion 136' includes a substrate 400' on which a thick field oxide 658' has been grown. Overlying the thick field oxide 658' is a transducer area 416' whose outer surface has been modified with recessed areas 664. The recessed portion 136' of dielectric layer 652' overlying the transducer area 416' has recesses 664 formed in its outer surface. These recesses 664 may also extend beyond the edges of the transducer area 416' at least so far as the surface of the ball 136' may be exposed to the desired medium.

The purpose of the recesses 664 is to inhibit tissue adhesion to the surfaces of the ball 136' that are exposed to the medium to be measured. Tissue adhesion is known to occur on the surfaces of implants through the attachment of fibroblasts. This phenomenon is well known and is described in Von Recum et al., "Surface Roughness, Porosity, and Texture as Modifiers of Cellular Adhesion," *Tissue Engineering*, Vol. 2, No. 4, 1996 (available from the Dept. of Bioengineering, Clemson University, Clemson, S.C.). The recesses 664 are presently preferred to be about one micron deep, three microns wide, and spaced three microns apart in a checkerboard topography. Such recesses can be fabricated by conventional selective etching techniques adapted to the spherical shape of the ball 136.

Figure 7:
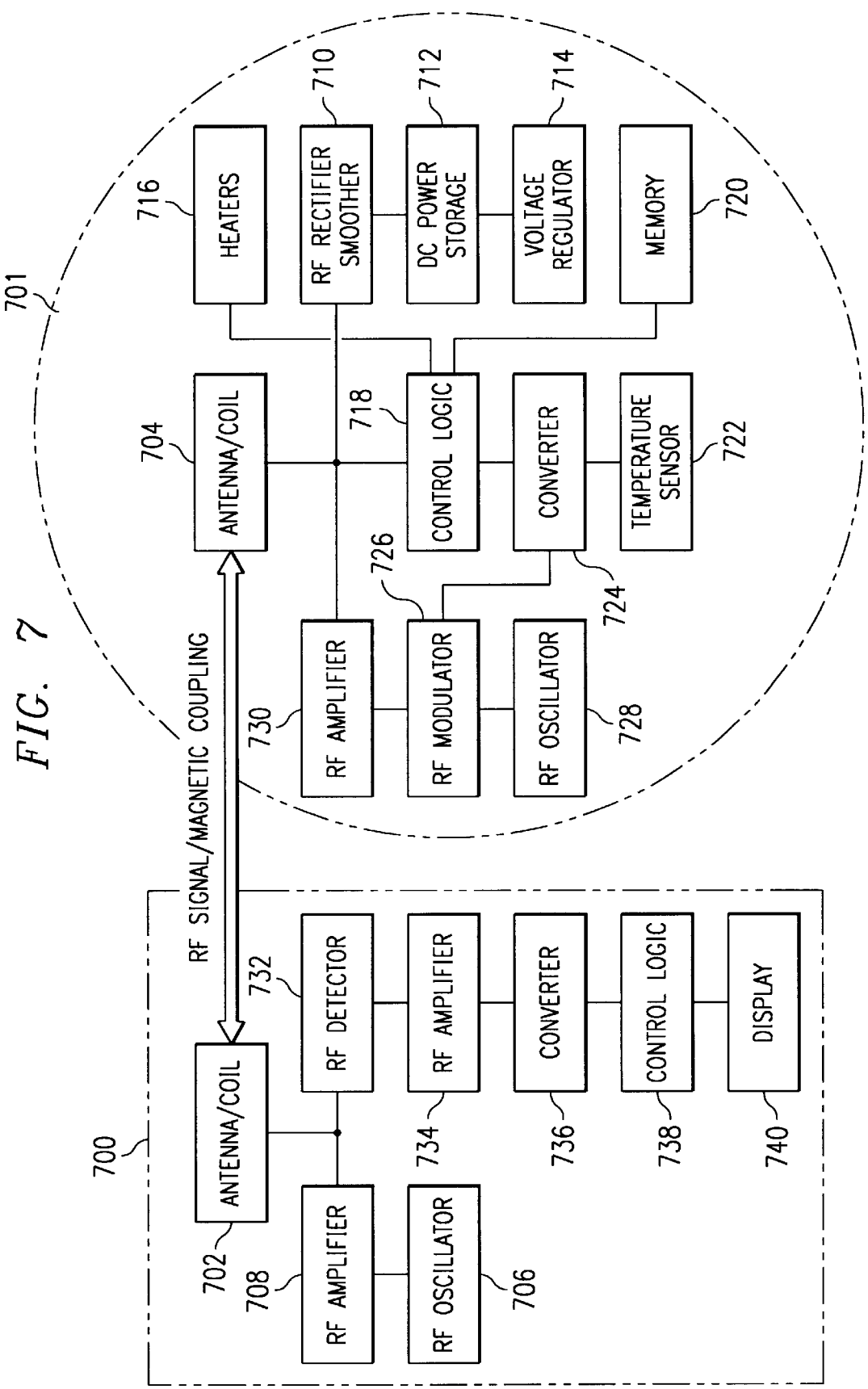
FIG. 7 illustrates an alternative embodiment of a block diagram of the control system and a thermal-sensing ball.

Referring now to FIG. 7, there is illustrated an alternative embodiment of a block diagram of the control system and a thermal-sensing ball. A control system 700 (similar to control system 110) includes an antenna/coil 702 that transmits RF power to an antenna/coil 704 of a ball 701. Power is transported either by RF radiation or by magnetic coupling between the control system antenna/coil 702 and ball antenna/coil 704. Control system 700 generates RF power with an RF oscillator 706 coupled to an RF amplifier 708. The RF amplifier 708 is coupled to the control system antenna/coil 702. RF power received at antenna/coil 704 of ball 701 is rectified and smoothed by an RF rectifier smoother 710 coupled to the antenna/coil 704. The RF rectifier smoother 710 converts RF energy to a DC voltage. The DC power is stored in a DC power storage unit 712, which may be a capacitor, a battery, or the combination thereof. The capacitor of the DC power storage unit 712 may be included in the smoothing portion of RF rectifier smoother 710. A voltage regulator 714 is coupled to the DC power storage unit 712 to regulate the DC voltage in order to provide stable voltage for powering the ball 701 for any condition or distance between control system 700 and the ball 701. The voltage regulator 714 supplies DC voltage to all circuits of ball 701, in a manner well-known to those skilled in the art.

A heater section 716 is controlled through a control logic section 718 (similar in operation to the microprocessor 338), which switches power from the antenna/coil 704 through to the heater section 716 according to either received or programmed commands. The switching function (similar to switches 404, 406, and 408) is illustrated as part of the control logic 718. The control logic 718 may be configured to control the activity of all the circuits on ball 701. The control logic 701 may be a microcontroller, a digital signal processor, or any other processor suitable to the size constraints and functions required to be processed. The control logic 718 interfaces to a memory 720 for storing information, and reading information therefrom on command from the external control system 700. One or more temperature sensors 722 (similar in operation to the sensor 344) measure the temperatures associated with the heater section 716, which heater section 716 may comprise one or more heating elements fabricated at various locations on the thermal-sensing ball 701. The output of the temperature sensor 722 is converted to digital data via an A/D converter 724 (similar to A/D converter 346). The converter 724 is controlled by the control logic 718, and connects to an RF modulator 726 for modulation of the digital data onto an RF carrier signal generated by an RF oscillator 728 for transmission for the ball 701. The modulated signal from the RF modulator 726 is amplified using an RF amplifier 730 to obtain sufficient signal strength for coupling from the ball 701 to the control system 700.

The frequency of RF oscillator 728 is preferably not the same as the frequency generated by RF oscillator 706 of control system 700. The RF signal produced by RF oscillator 728 is modulated with the signal produced by converter 724 in the RF modulator 726. The ball 701 may operate under AM, FM, PM, or any other analog and digital modulation methods. The information transmitted from the ball 701 is received at the control system antenna/coil 702. The received RF signal is detected by an RF detector 732 and amplified by an RF amplifier 734. The amplified signal is converted to a digital signal by an A/D converter 736. The converter 736 is coupled to control logic 738 (similar to the control functions provided by the CPU 112), which processes the data received from ball 701, and controls a display 740 and other electrical circuitry of control system 700. The display 740 provides audio and visual signaling to a human operator, with the visual aspect being as simple as an LED, or as complex as a computer display, or it may simply be an interface to other instrumentation equipment.

Figure 8:
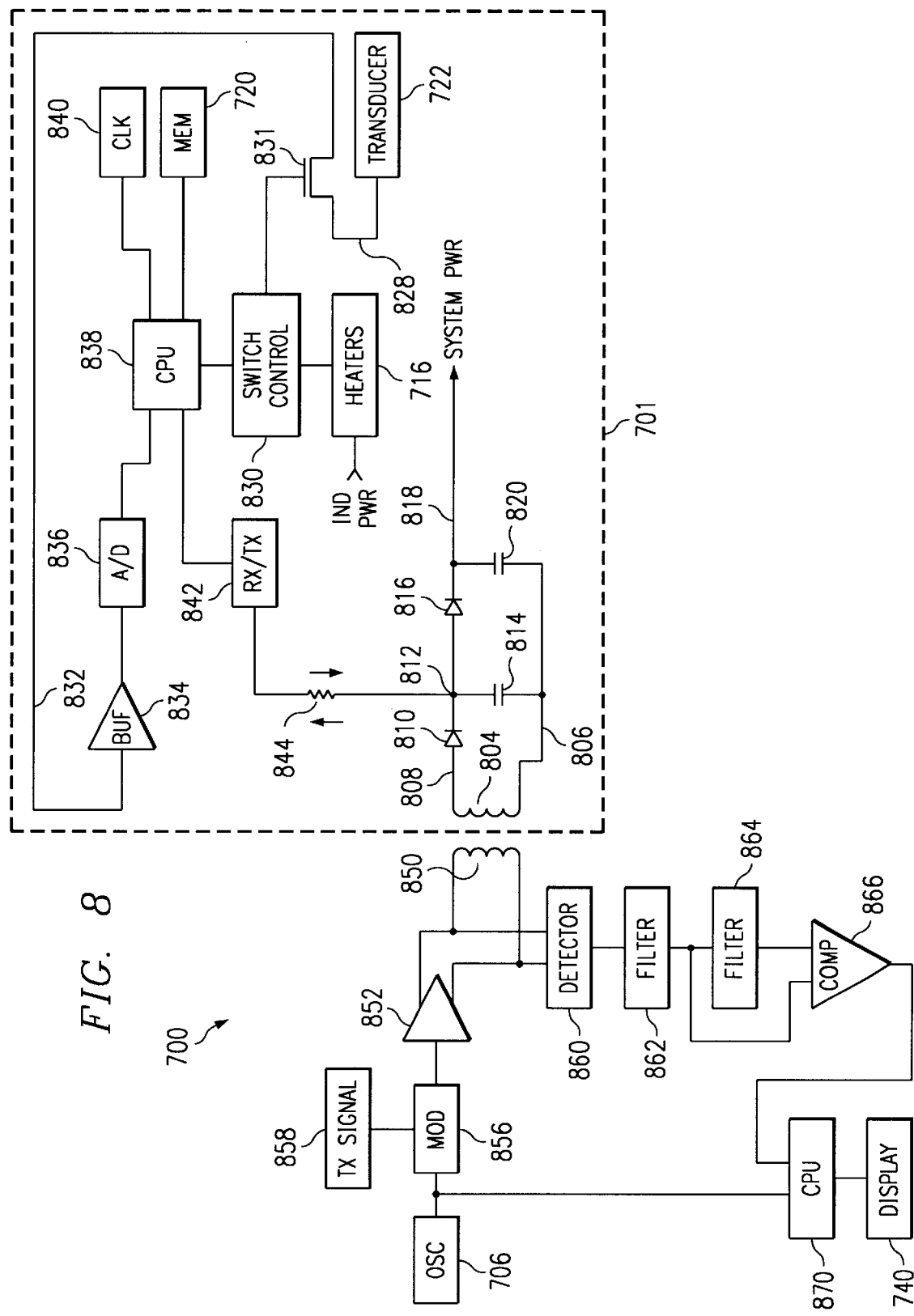
FIG. 8 illustrates a schematic block diagram of an alternative embodiment of the monitoring station and thermal-sensing ball of FIG. 7.

Referring now to FIG. 8, there is illustrated a schematic block diagram of the alternative embodiment of the monitoring station and thermal-sensing ball of FIG. 7. The ball 701, as described hereinabove, is operable to provide a transducer 722 for interfacing with the desired quantitative condition. The illustrated alternative embodiment is that associated with a "passive" system, which term refers to a system having no battery associated therewith. In order to operate the system, there is provided an inductive coupling element 804 in the form of an inductor, which is operable to pick up an alternating wave or impulse via inductive coupling, and extract the energy therein for storage in the inductive element 804. This will create a voltage across the inductive element 804 between a node 806 and a node 808. A diode 810 is connected between the node 808 and the node 812, with the anode of diode 810 connected to node 808 and the cathode of diode 810 connected to a node 812. Typically, the diode 810 will be fabricated as a Schottky diode, but can be a simple PN semiconductor diode. For the purposes of this embodiment, the PN diode will be described, although it should be understood that a Schottky diode could easily be fabricated to replace this diode. The reason for utilizing a Schottky diode is that the Schottky diode has a lower voltage drop in the forward conducting direction.

The diode 810 is operable to rectify the voltage across the inductive element 804 onto the node 812, which has a capacitor 814 disposed between node 812 and node 806. Node 812 is also connected through a diode 816 having the anode thereof connected to node 812 and the cathode thereof connected to a node 818 to charge up a capacitor 820 disposed between node 818 and 806. The capacitor 820 is the power supply capacitor for providing power to the ball 701. The capacitor 814, as will be described hereinbelow, is operable to be discharged during operation of the system and, therefore, a separate capacitor, the capacitor 820, is required for storing power to power the system of the ball 701.

There is also provided a switching transistor 831 which has one side of the gate/source path thereof connected to a node 828 which is the output of the transducer 722, and the other side thereof connected to a node 832. The gate of transistor 831 is connected to the output of a switch control 830. Node 832 is connected to the input of a buffer 834 to generate an analog signal output thereof which is then converted with an analog-to-digital converter 836 to a digital value for input to a CPU 838. The CPU 838 is operable to receive and process this digital input voltage. A clock circuit 840 is provided for providing timing to the system. The memory 720 is provided in communication with the CPU 838 to allow the CPU 838 to store data therein for later transmittal back to the control system 700 or for even storing received instructions. This memory 722 can be volatile or it can be non-volatile, such as a ROM. For the volatile configuration, of course, this will lose all information when the power is removed. The CPU 838 is operable to provide control signals to the switch control 830 for turning on the transistor 831 at the appropriate time. In addition to the transistor 831 being toggled to read the transducer 722, transistor 831 could be a pass-through circuit such that the CPU 838 can continually monitor the voltage at the output of the transducer 722. The CPU 838 also controls the flow of power to one or more heater circuits 716 through the switch control 830. System power to all power-consuming elements of the ball 701 is provided at the SYSTEM PWR output node. The power to the heater elements 716 is provided as described hereinabove with reference to FIG. 3B and supply 354.

The memory 720, in conjunction with the operation of the CPU 838, can be operated such that a temperature history can be stored for the one or more internal temperature sensors 722. For example, if the internal thermometer in the form of the transducer 722 were ingested and passed through the gut, a temperature history could be recorded at set times. Similarly, a temperature profile of the tumor 122 during ablation could be recorded and uploaded to the control system 700 for analysis. This would require a time base, which is provided by RF oscillator 728 (illustrated herein as part of a transmit/receive circuit 842) and which would comprise an integral part of the operation of the CPU 838. This allows information in the form of temperature measurements to be taken at certain times. In one embodiment, once the transducer 722 is eliminated from the body, it can then be "scanned" and the information stored therein downloaded. Further, this temperature information may only be stored temporarily until a download operation, at which time the memory 720 is cleared and new data is taken. This would allow the memory 720, which may be limited in capacity, to be cleared periodically.

In order to communicate with the CPU 838 for transferring data thereto and for allowing the CPU 838 to transfer data therefrom, the receive/transmit circuit 842 is provided for interfacing to node 812 through a resistive element 844. This allows RF energy to be transmitted to node 812. It is important to note that the semiconductor junction across diode 810 is a capacitive junction. Therefore, this will allow coupling from node 812 to node 808. Although not illustrated, this could actually be a tuned circuit, by selecting the value of the capacitance inherent in the design of the diode 810. In any event, this allows an RF connection to be provided across diode 810 while allowing sufficient energy to be input across inductive element 804 to provide a voltage thereacross for rectification by the diode 810 and capacitor 814. Typically, the frequency of this connection will be in the MHz range, depending upon the design. However, many designs could be utilized. Some of these are illustrated in Beigel, U.S. Pat. No. 4,333,072, entitled "Identification Device," issued Jun. 1, 1982, and Mogi et al., U.S. Pat. No. 3,944,982, entitled "Remote Control System For Electric Apparatus," issued Mar. 16, 1976, which are incorporated herein by reference. With these types of systems, power can continually be provided to the node 812 and subsequently to capacitor 820 to allow power to be constantly applied to the ball 701.

The control system 700 which is disposed outside of the body and proximate to the ball 701 includes an inductive element 850 which is operable to be disposed in an area proximate to the skin, yet exterior to the body, in the proximity of the ball 701. The inductive element 850 is driven by a driving circuit 852 which provides a differential output that is driven by an oscillator 706. This will be at a predetermined frequency and power level necessary to couple energy from inductive element 850 to inductive element 804. Since this is an external system, the power of the oscillator can be set to a level to account for any losses through the body tissues. To allow information to be transmitted, a modulation circuit 856 is provided which is modulated by a transmitter signal in a block 858 that allows information to be modulated onto the oscillator signal of the oscillator 706, which oscillator signal is essentially a "carrier" signal. However, it should be understood that the information that is transmitted to the ball 701 could merely be data information, whereas the CPU 838 could operate independent of any transmitted information to provide the temperature output. Alternatively, entire control of the system could be provided by the transmit signal 858 and the information carried thereon, since power must be delivered to the illustrated embodiment due to the lack of any independent power in the ball 701.

When the information is received from the ball 701, it is superimposed upon the oscillator signal driving the inductive element 850. This is extracted therefrom via a detector 860 which has the output thereof input to a first low pass filter 862, and then to a second low pass filter 864. The output of low pass filters 862 and 864 are compared using a comparator 866 to provide the data. The filter 862 provides an average voltage output, whereas the filter 864 provides the actual digital voltage output. The output of the comparator 866 is then input to a CPU 870 which also is powered by the oscillator 706 to process the data received therefrom. This can then be input to a display 740.

Referring now to FIGS. 9A–9C, there are illustrated alternate embodiments for the transmit/receive operation. In FIG. 9A, there is provided an oscillator 900 which drives an external inductive element 902. Typically, there is some type of load 904 disposed across the inductive element 902. This is the primary power that is provided to the system. A separate inductive element 906 is provided on the ball 701, for being inductively coupled to the inductive element 902. Thereafter, a voltage is generated across the inductive element 906, the inductive element 906 being connected between nodes 908 and 910. A diode 912 is connected between node 908 and a power node 914, and a power supply capacitor 916 is disposed across node 914 and a node 910. This allows the voltage on node 908 to be rectified with diode 912.

In FIG. 9B, the receive operation, in this alternative embodiment, utilizes a separate inductive clement or antenna 924 in the ball 701, which is operable to be connected between nodes 909 and 911. Node 909 is capacitively coupled to a transmit node 930 with a capacitor 932, the capacitor 932 being a coupling capacitor. A transmitter 934 is provided for transmitting received data from a line 936 to the node 930, which is then coupled to the node 909 to impress the RF signal across the inductive element 924. A corresponding inductive element 940 is disposed on the external remote controller of control system 700, which inductive element 940 is operable to be disposed proximate to the inductive clement 924, but external to the human body. The inductive element 940 is basically a "pick-up" element which is operable to receive information and function as an antenna, and provide the received signal to a receiver 942. The structure of FIG. 9B is a separate structure, such that node 909 is isolated from node 908, the power receiving node. However, it should be understood that any harmonics of the oscillator 900 would, of course, leak over into the inductive element 924. This can be tuned out with the use of some type of tuning element 944 on the ball 701 disposed across inductive element 924, and also a tuning element 946 disposed across the inductive element 940, i.e., the antenna.

Referring now to FIG. 9C, there is illustrated a simplified schematic diagram of the receive portion. The ball 701 has associated therewith a separate receive antenna or inductive element 950 disposed between node 913 and a node 952. Node 952 is capacitively coupled to a receive node 954 with a coupling capacitor 956. A receiver 958 is provided for receiving the information transmitted thereto and providing on the output thereof data on a data line 960. The receiver 958 is operable to receive the RF signal, demodulate the data therefrom, and provide digital data on the output 960. External to the human body and the ball 701 is a transmitter 962 which is operable to impress a signal across an external inductive element 964. The inductive element 964 basically provides the RF energy and is essentially tuned with a tuning element 966. A corresponding tuning element 968 is provided on the ball 701 and disposed across inductive element 950, the inductive element 950 acting as an antenna, as well as the inductive element 964.

Note that in circumstances where the signals of ball 701 cannot be adequately received therefrom and/or power coupled thereto, the signal coupling head of the control system 700 may need to be inserted into the body proximate to the ball 701 in order to couple the transmit/receive signals and power. Furthermore, where more than one ball 701 is used, communication of power and data signals between the various ball 701 may need to employ distinct time periods (i.e., time multiplexing) when communication occurs using a single common frequency, or discrimination circuits may need to be used where communication occurs simultaneously with the plurality of implanted balls 701 having different oscillator frequencies.

Referring now to FIG. 10, there is illustrated a side view of an alternative embodiment utilizing additional circuitry or structure attached to the ball 701 for providing a local power source. As described hereinabove, the ball 701 requires a power-generating structure for storing a power supply voltage such that diodes must be provided for receiving and rectifying a large amount of power and charging up a power supply capacitor. Alternatively, the thermal-sensor ball 701 could be configured to interface to an attached power supply system 1000 comprising either a battery or a capacitor. The local power supply system 1000 is illustrated as disposed on a circuit board 1003 defined by supporting structures 1002 and 1004. The circuit board 1003 contains electronics for interfacing the local power supply system 1000 to the ball 701. The entire structure of FIG. 10 would be encapsulated, with only a thin layer thereof disposed over ball 701.

Referring now to FIG. 11, there is illustrated a block diagram of the ball 701 using a battery as the local power supply system 1000. A battery 1101 is provided as a source of self-contained power and is connected across a capacitor 1100 to providing smoothing of any power output to the system power-consuming elements of the ball 701. Power for all on-board components is obtained from the SYSTEM POWER output by providing sufficient charge to the capacitor 1100. The capacitor 1100 could be formed on the surface of the ball 701 or it could actually be part of the battery structure 1101. Additionally, the capacitor 1100 could actually be the capacitance of the battery 1101. Additional structure could be provided for powering the CPU 838 and the other circuitry on the ball 701 from the battery 1101. As such, there would only be required a smaller inductive element 1102 and a capacitor 1104 to allow the receive/transmit block 842 to receive/transmit information from and to the exterior control system 700. The switch control 830 controls the gate of the switching transistor 831 to switch the output of the transducer 722 through the switching transistor 831 source/drain path to the CPU 838. The CPU 838 switches received power through the switch control 830 to one or more heaters 716 on the ball 701. The memory 720 contains stored information which comprises a unique ID, and perhaps patient and physician information, etc.

Figure 12:
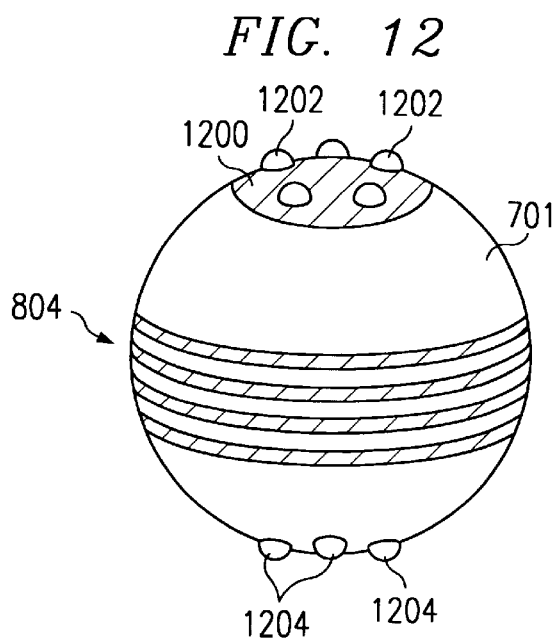
FIG. 12 illustrates a perspective view of a thermal-sensor ball having a single transducer interface, an inductive element is illustrated as being strips of conductive material wrapped around the exterior of the ball.

Referring now to FIG. 12, there is illustrated a perspective view of a ball 701 having a single transducer interface and the inductive element 804 (inductive element 1102 being similar thereto) is illustrated as being strips of conductive material wrapped around the exterior of the ball 701. The inductive element 804 is formed of a conductive strip wrapped many times around the ball 701. The length of inductive element 804 depends upon the receive characteristics that are required. As described hereinabove with reference to FIGS. 9A–9C, there could be multiple conductive strips, each associated with a receive function, a transmit function, or a power function, or they could all share one single conductive element or strip. On one end of the ball 701 there is provided a transducer interface 1200 of the transducer 722 having, optionally, one or more interface balls 1202 (or partial balls, called nodules) associated therewith extending from the transducer interface surface to provide enhanced engagement of the measuring surface or physical entity and also utilized to more effectively transmit heat to the surrounding medium. The interface balls 1202 can be made of non-reactive material, e.g., gold to prevent degradation while in the body. Note that in some applications, the interface nodules 1202 are not required for obtaining the desired quantitative data, but can be used to transmit heat. On the other end of the ball 701 are provided interconnect balls 1204 (or nodules) for interconnecting to one or more other substantially spherical balls which may provide similar functions such as monitoring of quantitative data, or unique functions such as supplying only power or data buffering and storage.

Figure 13:
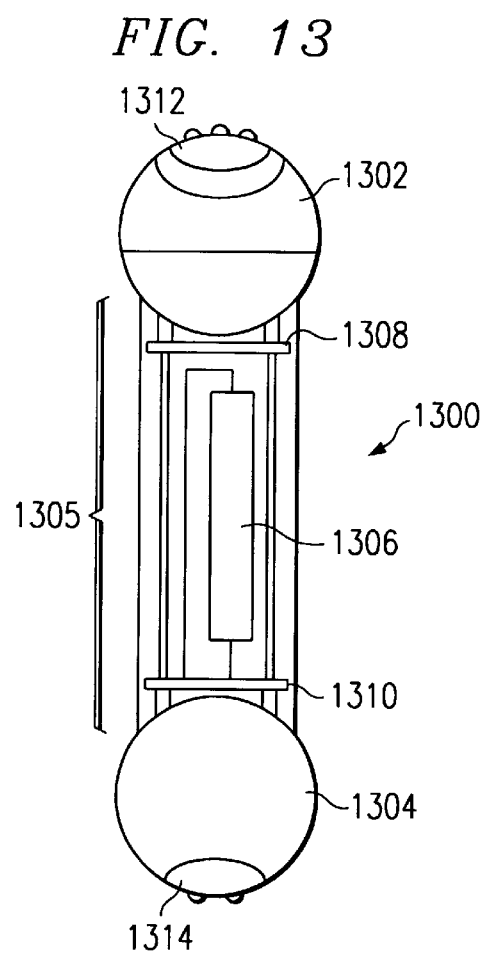
FIG. 13 illustrates a side view of an alternate embodiment having additional circuitry where the ball provides an actuator function to stimulate the tumor tissues.

Referring now to FIG. 13, there is illustrated a side view of an alternate embodiment having additional circuitry where the ball provides an actuator function to stimulate the tumor tissues. In one application, the actuator 1300 comprises two primary ball structures 1302 and 1304 which provide anode and cathode stimulation means, a power supply generating structure 1306 connecting the ball structures 1302 and 1304 for storing and providing a power supply voltage to the ball structure 1302 and 1304. Rectifying elements provided on the balls 1302 and 1304 (e.g., diodes, and not shown) must be provided for receiving and rectifying the power, and charging up a power supply capacitor, in addition to a main "surge" capacitor for providing a relatively large amount of pulsed energy, if such pulsed energy is desired for the particular application. The structure 1305 between the balls 1302 and 1304 may contain either a battery or a capacitor 1306 for providing stand-alone power for the assembly. This is disposed between interface supporting structure 1308 and 1310. The two primary balls 1302 and 1304 have respective output pad interfaces 1312 and 1314, respectively, for contacting the desired medium for stimulation.

Figure 14:
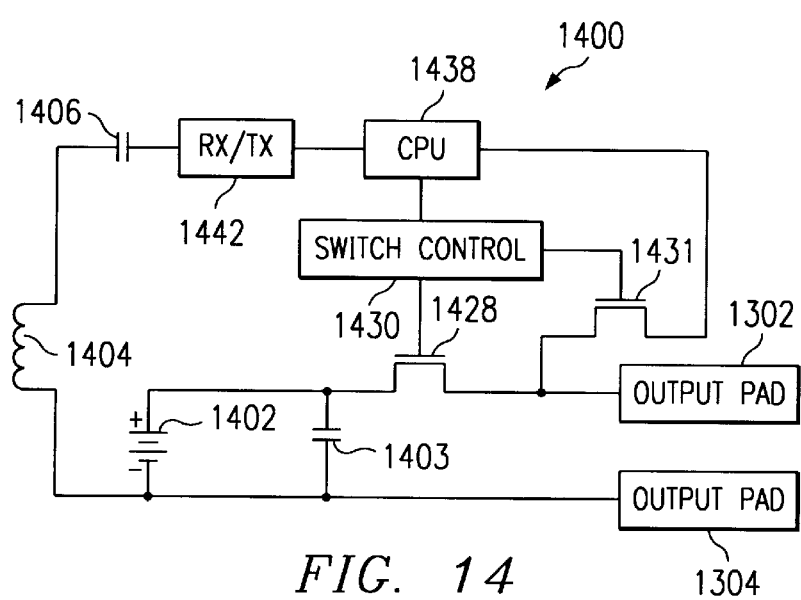
FIG. 14 illustrates a general block diagram of the actuator circuit with the use of a battery.

Referring now to FIG. 14, there is illustrated a general block diagram of the actuator circuit with the use of a battery. The actuator circuit 1400 comprises a battery 1402 which is connected to a capacitor 1403. The battery 1402 is provided across the capacitor 1403 to provide sufficient charge therefor. Additionally, the capacitance 1403 could actually be the capacitance of the battery 1402. Additional structure could be provided for powering a CPU 1438 and the other circuitry on the ball 700 from the battery 1402. As such, there would only be required a smaller inductive element 1404 and a capacitor 1406 to allow the receive/transmit block 1442 to receive/transmit information from and to the external control system 700. The CPU 1438 controls a switch control circuit 1430, which in turn switches transistors 1428 and 1431 on or off. Turning transistor 1438 on, switches power to the stimulation output pad 1302, and drives the energy across the contacted medium to the return output pad 1304.

Figure 15:
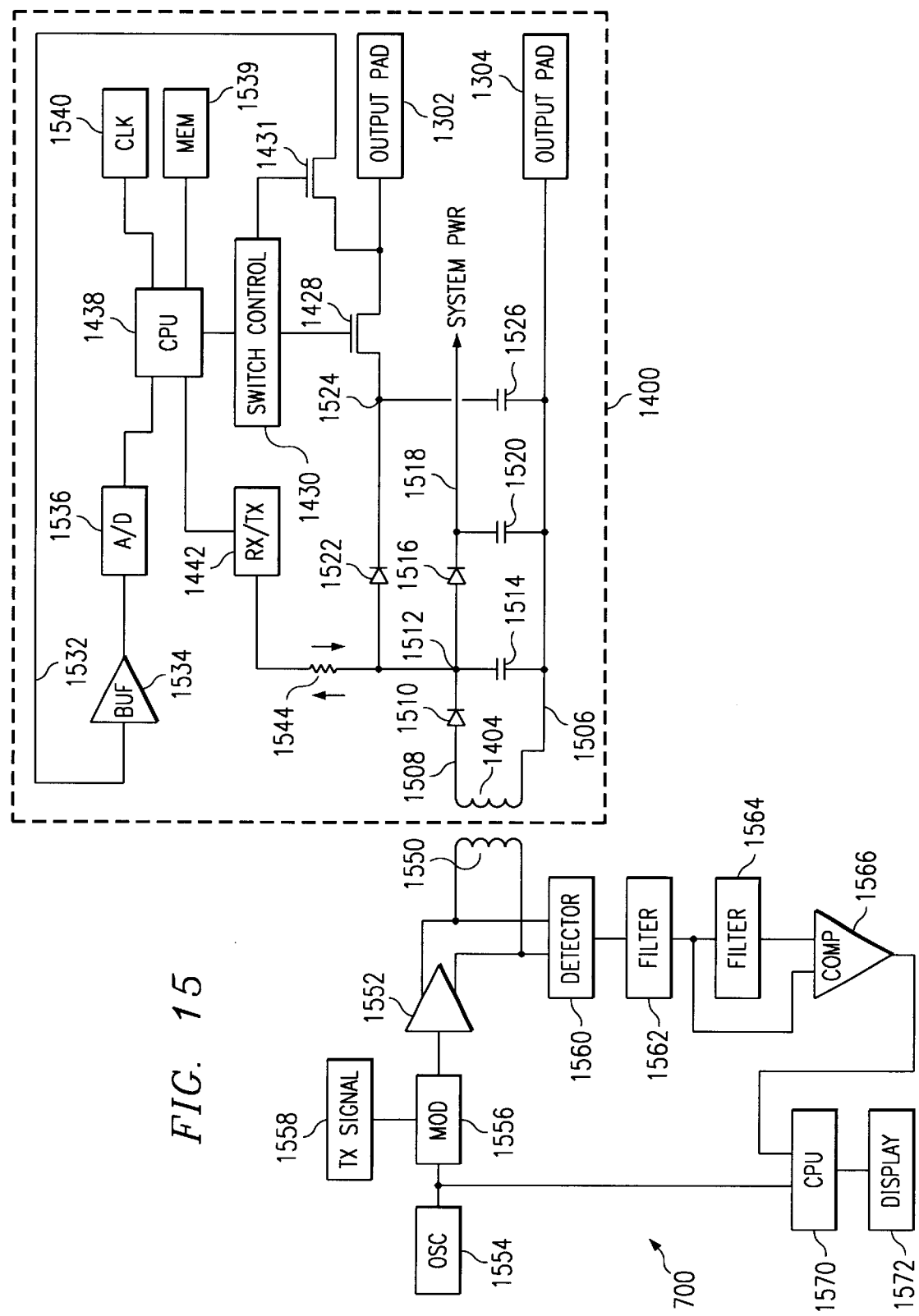
FIG. 15 illustrates a more detailed schematic block diagram of the actuator circuit and the external control system for the powering/detection operation.

Referring now to FIG. 15, there is illustrated a more detailed schematic block diagram of the actuator circuit and the external control system for the powering/detection operation. The actuator circuit 1400 is operable to provide two output interfaces, the output pad 1302 as an anode and the output pad 1304 as a cathode, for interfacing with the medium to be stimulated. The spacing between these two pads or contacts 1302 and 1304 is approximately 0.5 cm. The illustrated embodiment is that associated with a "passive" system, which term refers to the fact that there is no battery associated therewith. In order to operate the system, there is provided the inductive coupling element 1404 in the form of an inductor, which is operable to pick up an alternating wave or impulse via inductive coupling and extract the energy therein for storage in the inductive element 1404. This will create a voltage across the inductive element 1404 between a terminal 1506 and a terminal 1508. A diode 1510 is connected between the node 1508 and a node 1512, with the anode of diode 1510 connected to node 1508 and the cathode of diode 1510 connected to a node 1512. Typically, the diode 1510 will be fabricated as a Schottky diode, but can be a simple PN semiconductor diode. For the purposes of this embodiment, the PN diode will be described, although it should be understood that a Schottky diode could easily be fabricated to replace this diode. The reason for utilizing a Schottky diode is that the Schottky diode has a lower voltage drop in the forward conducting direction.

The diode 1510 is operable to rectify the voltage across the inductive element 1404 onto the node 1512, which has a capacitor 1514 disposed between node 1512 and node 1506. Node 1512 is also connected through a diode 1516 having the anode thereof connected to node 1512 and the cathode thereof connected to a node 1518 to charge up a capacitor 1520 disposed between node 1518 and 1506. The capacitor 1520 is the power supply capacitor for providing power to the actuator circuit 1400. The capacitor 1514, as will be described hereinbelow, is operable to be discharged during operation of the system and, therefore, a separate capacitor, the capacitor 1520, is required for storing power to power the system.

The node 1512 is connected to the anode of a diode 1522, the cathode thereof connected to a node 1524. A main capacitor 1526 has one side connected to node 1524 and the other side thereof connected to node 1506. The capacitor 1526, as will be described hereinbelow, is operable to provide the primary discharge energy to, for example, the myocardium or any other tissue to which a stimulus may be applied, via the output pad 1302, the anode of the actuator circuit 1400. This node 1524 is connected to one side of the gate/source path of a drive transistor 1428, the other side thereof connected to the output pad 1302. The gate of drive transistor 1428 is connected to the output of a switch control circuit 1430. Drive transistor 1428 is operable to be turned on for a short period of time to connect to the top plate of capacitor 1526 to the output pad 1302, and subsequently, to conduct current to the desired tissue.

In addition to transmitting energy out on output pad 1302, there is also provided a sense transistor 1431 which has one side of the gate/source path thereof connected to the output pad 1302 and the other side thereof connected to a node 1532. The gate of sense transistor 1431 is connected to the output of the switch control 1430. Node 1532 is connected to the input of a buffer 1534 to generate an analog signal output thereof which is then converted with an analog-to-digital converter 1536 to a digital value for input to a CPU 1438. The CPU 1438 is operable to receive and process this digital input voltage. A clock circuit 1540 is provided for providing timing to the system. A memory 1539 is provided in communication with the CPU 1438 to allow the CPU 1438 to store data therein for later transmittal back to the control system 700 or for even storing received instructions. This memory 1539 can be volatile or it can be non-volatile, such as a ROM. For the volatile configuration, of course, this will lose all information when the power is removed.

The CPU 1438 is operable to provide control signals to the switch control 1430 for turning on the drive transistor 1428 or the sense transistor 1431 at the appropriate time. Typically, the drive transistor 1428 is controlled to turn on for a period of approximately 0.5 microseconds 60–80 times per minute. Once drive transistor 1428 is turned off, then sense transistor 1431 can be turned on. Alternatively, sense transistor 1431 could be a pass-through circuit such that the CPU 1438 can always monitor the voltage on the output pad 1302. However, it is desirable with the sense transistor 1431 and the sensing operation to sense depolarization in the desired tissue after an output voltage has been provided thereto for a short duration of time.

In order to communicate with the CPU 1438 for transferring data thereto and for allowing the CPU 1438 to transfer data therefrom, the receive/transmit circuit 1442 is provided for interfacing to node 1512 to a resistive element 1544. This allows RF energy to be transmitted to node 1512. It is important to note that the semiconductor junction across diode 1510 is a capacitive junction. Therefore, this will allow coupling from node 1512 to node 1508. Although not illustrated, this could actually be a tuned circuit, by selecting the value of the capacitance inherent in the design of the diode 1510. In any event, this allows an RF connection to be provided across diode 1510 while allowing sufficient energy to be input across conductive element 1404 to provide a voltage thereacross for rectification by the diode 1510 and capacitor 1514. Typically, the operating frequency of this connection will be in the MHz range, depending upon the design of which a variety are possible. For example, some possible designs are illustrated in U.S. Pat. No. 4,333,072 entitled "Identification Device," issued Jun. 1, 1982, and Mogi et al., U.S. Pat. No. 3,944,982, entitled "Remote Control System For Electric Apparatus," issued Mar. 16, 1976. With these types of systems, power can continually be provided to the node 1512 and subsequently to capacitors 1520 and 1526 to allow power to be constantly applied to the actuator circuit 1513. The diode 1522 may not be required in order to provide the sufficient charge to capacitor 1526, but some type of isolation is required between the capacitor 1526 and the capacitor 1520. Voltage regulation may also be required in order to provide a shaped pulse on the output pad 1302. This could be provided by the switch control 1430.

The control system 700 which is disposed external to the body and proximate to the actuator circuit 1400 includes an inductive element 1550 which is operable to be disposed in an area proximate to the skin exterior to the body in the proximity of the actuator circuit 1400. The inductive element 1550 is driven by a driving circuit 1552 which provides a differential output that is driven by an oscillator 1554. This will be at a predetermined frequency and power level necessary to couple energy from inductive element 1550 to inductive element 1404. Since this is an external system, the power of the oscillator can be set to a level to account for any losses through the body tissues. To allow information to be transmitted, a modulation circuit 1556 is provided which is modulated by a transmitter signal in a block 1558 that allows information to be modulated onto the oscillator signal 1554, which oscillator 1554 provides a "carrier" signal. However, it should be understood that the information that is transmitted to the actuator circuit 1513 could merely be date information whereas the CPU 1438 could operate independent of the information being transmitted to provide the correct timing and wave shape for the output pulses. Alternatively, the entire control of the system may be provided by the transmit signal 1550 and the information carried thereon, because power must be delivered to the illustrated embodiment when there is a lack of an independent power source in the actuator circuit 1400.

The information received from the actuator circuit 1400 is modulated upon the oscillator signal driving the inductive element 1550. This information is extracted therefrom via a detector 1560 which has the output thereof input to a first low pass filter 1562 and then to a second low pass filter 1564. The output of low pass filters 1562 and 1564 are compared with a comparator 1566 to provide the data. The filter 1562 will provide an average voltage output, whereas the filter 1564 will provide the actual digital voltage output. The output of the comparator 1566 is then input to a CPU 1570 which also is powered by the oscillator 1554 to process the data received therefrom. This can be input to a display 1572.

Figure 16:
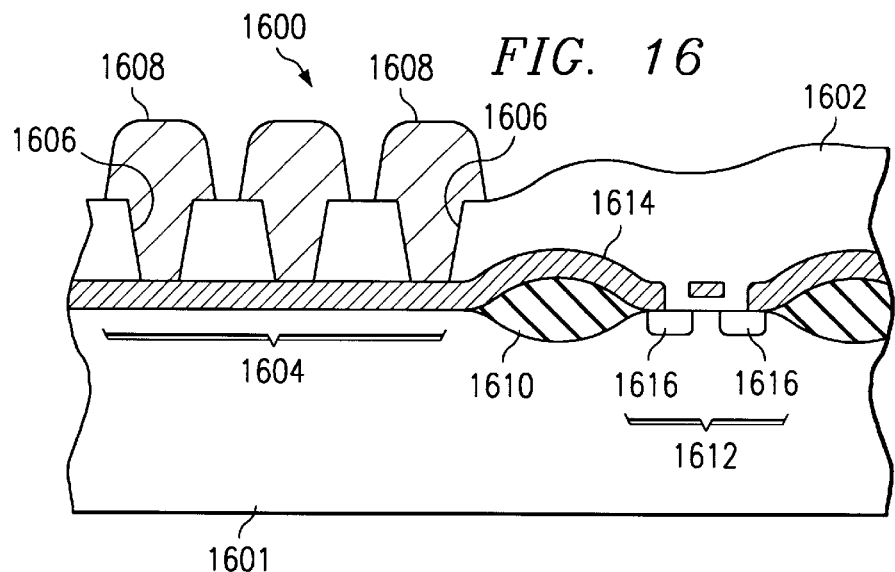
FIG. 16 illustrates a cross-sectional view of an output pad of the actuator embodiment.

Referring now to FIG. 16, there is illustrated a cross-sectional view of an output pad of the actuator embodiment. In general, an output pad 1600 (similar to output pad 1302) is required to provide a conductive interface between the transistor 1428 and, for example, the medium which is to be stimulated. This therefore requires some type of metallic interface that is non-reactive. Such an interface would require a metal such as gold, platinum and the like. In the disclosed embodiment, gold would be provided.

After the formation of the upper metal layer via a deposition technique with metal such as aluminum or copper, a passivation layer of oxide 1602 is disposed over the substrate to basically prevent oxidation of the metal layers and protect the semiconductor circuits in general. The contact layer 1614 extends beyond the active region 1612 to an output pad region 1604 and is separated from the active region 1612 by a layer of field oxide 1610 or some type of isolation oxide. There may be some type of channel stop implant disposed below the field oxide layer 1610. The contact 1614 extends from the source/drain implant 1616 to the region 1604. This contact 1614 is required to be fairly conductive. Typically, polycrystalline silicon is not of sufficient conductivity to meet this requirement. Therefore, some type of polysilicide process will be required, wherein the upper surface is converted to some type of silicide such as titanium disilicide to lower the surface resistivity thereof. Alternatively, a metal layer could be provided which is connected to the contact region 1614.

Once the contact 1614 is formed and the passivation layer 1602 is disposed over the entire structure, vias 1606 are formed therein. These vias are then filled with metallic plugs 1608 by forming a layer of metal over the layer 1602 and then etching the layer 1602 to remove the undesired portions. The metal plugs 1608 may be formed of metal such as aluminum or gold. If they were formed of gold, this would allow for soldering if they were to be used as contacts. However, in this context, these plugs 1608 are utilized for conductivity purposes. Therefore, an aluminum plug would be sufficient if it were covered with a thin layer of gold to render the aluminum non-reactive and prevent oxidation thereof. Alternatively, in the disclosed embodiment, the plug 1608 may, of course, be gold. However, it should be understood that any type of non-reactive metal could be utilized as long as the surface thereof is sufficiently non-reactive, and the conductance of the plug 1608 is sufficiently high to result in a low resistance path between the exterior of the spherical IC and a capacitive plate (not shown). The reason for this is that the stored charge must be discharged into a resistance as low as 500 Ohms and any significant resistance disposed between the upper plate of the capacitor and the exterior must be minimized.

Figure 17A:
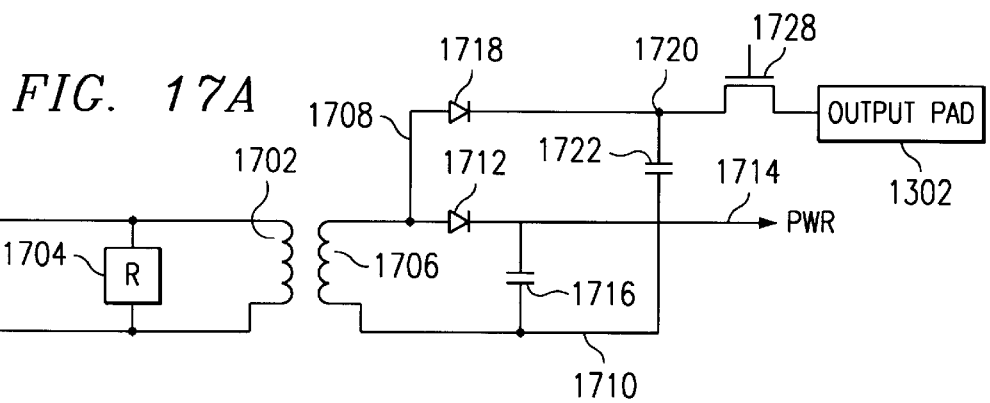
FIGS. 17A–17C illustrates alternate embodiments for the transmit/receive operation of the actuator embodiment.
Figure 17B:
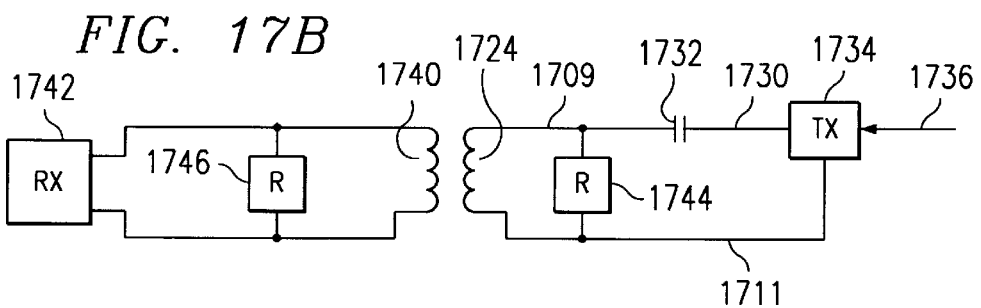
Figure 17C:
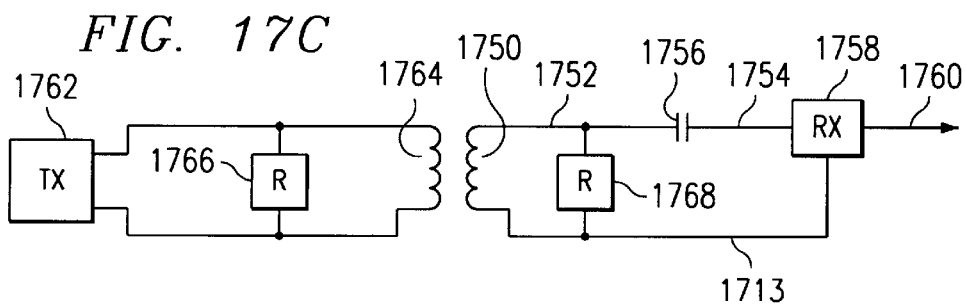

Referring now to FIGS. 17A–17C, there are illustrated alternate embodiments for the transmit/receive operation of the actuator embodiment. In FIG. 17A, there is provided an oscillator 1700 which drives an external inductive element 1702 which may be utilized to couple both electrical power and information or data. Typically, there is some type of load 1704 disposed across the inductive element 1702. A separate inductive element 1706 (similar to inductive element 1404), inductively coupled to inductive element 1702, is provided on the actuator 1400. Voltage generated across the inductive element 1706, connected between a node 1708 and a node 1710 is applied across rectifier 1712 connected between node 1708 and a power node 1714. A power supply capacitor 1716 disposed across node 1714 and node 1710 stores the rectified voltage for use by the circuit. Similarly, a rectifier 1718 is connected between the node 1708 and a node 1720 which is connected to one side of a main "surge" capacitor 1722. The other side of capacitor 1722 is connected to node 1710. This capacitor 1722 is similar to the main "surge" capacitor 1526 in FIG. 15. A switch transistor 1728 (similar to switching transistor 1428) is provided for connecting the node 1720 to the output pad 1302.

In the alternative embodiment of FIG. 17B, the receive operation utilizes a separate inductive element or antenna 1724 in the ball actuator 1400, which is operable to be connected between nodes 1709 and 1711. Node 1709 is capacitively coupled to a transmit node 1730 with a capacitor 1732, the capacitor 1732 being a coupling capacitor. A transmitter 1734 is provided for transmitting received data from a line 1736 to the node 1730, which is then coupled to the node 1709 to impress the RF signal across the inductive element 1724.

A corresponding inductive element 1740 is disposed on the external remote controller of control system 700, which inductive element 1740 is operable to be disposed proximate to the inductive element 1724, but external to the human body. The inductive element 1740 is basically a "pick-up" element which is operable to receive information and function as an antenna, and provide the received signal to a receiver 1742. The structure of FIG. 17B is a separate structure, such that node 1709 is isolated from node 1708, the power receiving node. However, it should be understood that any harmonics of the oscillator 1700 would, of course, leak over into the inductive element 1724. This can be tuned out with the use of some type of tuning element 1744 on the ball actuator 1400 disposed across inductive element 1724, and also a tuning element 1746 disposed across the inductive element 1740, i.e., the antenna.

Referring now to FIG. 17C, there is illustrated a simplified schematic diagram of the receive portion. The ball actuator 1400 has associated therewith a separate receive antenna or inductive element 1750 disposed between node 1713 and a node 1752. Node 1752 is capacitively coupled to a receive node 1754 with a coupling capacitor 1756. A receiver 1758 is provided for receiving the information transmitted thereto and providing on the output thereof data on a data line 1760. The receiver 1758 is operable to receive the RF signal, demodulate the data therefrom, and provide digital data on the output 1760. External to the human body and the ball actuator 1400 is a transmitter 1762 which is operable to impress a signal across an external inductive element 1764. The inductive element 1764 basically provides the RF energy and is essentially tuned with a tuning element 1766. A corresponding tuning element 1768 is provided on the ball actuator 1400 and disposed across inductive element 1750, the inductive element 1750 acting as an antenna, as well as the inductive element 1764.

Note that, in circumstances where the signals of the thermal-sensing ball 136 cannot be adequately received therefrom and/or power coupled thereto, the antenna 118 of the external control system 110 may need to be inserted into the body proximate to the ball sensor 136 in order to couple the transmit/receive signals and power. Furthermore, where more than one sensor ball 136 is used, communication of power and data signals between the various ball sensors 136 may need to employ distinct time periods (i.e., time multiplexing) when communication occurs using a single common frequency, or discrimination circuits may need to be used where communication occurs simultaneously with the plurality of implanted ball sensors 136 having different oscillator frequencies.

In summary, there is disclosed a system for treating tumors using multiple spherical thermal balls, each approximately one millimeter in diameter and each having integrated circuits capable of receiving energy by radio frequency from a wireless external central processing unit. The balls are injected through catheters placed directly into the blood vessels feeding the tumor. The balls are then released into the tumor circulation and delivered to the tumor tissue, which becomes impregnated with multiple thermal balls. As an alternative method, delivery and placement of the thermal balls can be accomplished by injection through a needle or by any other direct placement method. The thermal balls are then heated to a predetermined temperature capable of killing tumor cells. The uniform distribution of the thermal balls in the tumor allows a homogeneous destruction of the tumor tissue. The balls may also have temperature sensors, which transmit the tumor temperature by radio frequency to the external central processing unit. Alternatively, separate temperature sensing balls can be injected into the tumor to report temperature back to the central processing unit. This temperature data will allow the physician to monitor the exact tumor temperature and guide the required amount of energy to obtain tumor ablation without significantly injuring the surrounding normal tissue, and is less painful to the patient, since vital tissues are left substantially in tact. Each thermal ball can have a unique serial number that can be transmitted for identification purposes.

Although the preferred embodiment has been described in detail, it should be understood that various changes, substitutions and alterations can be made therein without departing from the spirit and scope of the invention as defined by the appended claims.

What is claimed is:

1. A system for treating tumors, comprising:

a processing unit equipped with antenna means for transmitting and receiving signals, and including input control means and display means; and one or more miniature substantially spherical heater balls for being disposed proximate to the tumor, each said heater ball including one or more heater elements and integrated circuitry for controlling said heater elements to radiate heat to the adjacent tumor, said integrated circuitry including input/output data communication circuitry and signal processing circuitry for communicating with said processing unit to receive signals for the purpose of controlling the operation of said heater elements.

2. The system of claim 1, further comprising a catheter delivery system for injecting said one or more heater balls into the tumor.

3. The system of claim 2, wherein said heater balls are delivered to the tumor in a viscous slurry using said catheter delivery system.

4. The system of claim 1, wherein said heater balls each include a unique identification number, and said processing unit can uniquely address and separately control each said heater ball.

5. The system of claim 1, wherein said heater ball further comprise a temperature sensor for sensing the temperature parameter of said one or more heater elements.

6. The system of claim 5, further comprising an analog-to-digital converter on each said heater ball for converting said temperature parameter to digital data.

7. The system of claim 1, wherein said heater balls are delivered to the tumor in a viscous slurry using said catheter delivery system, said viscous slurry comprising a blend of said heater balls and temperature sensing balls wherein said heater balls deliver heat to the tumor according to control signals from said processing unit, and said temperature sensing balls measure the temperature parameters of the tumor, said temperature sensing balls include at least one temperature sensor and integrated circuitry, said integrated circuitry including input/output data communication circuitry for communicating with said processing unit to transmit temperature information thereto.

8. The system of claim 1, wherein said heater balls are implemented having a size which is sufficiently large to block vessels which provide fresh blood to the tumor.

9. The system of claim I, wherein said one or more heater balls are configured to provide electrical stimulation to the tumor.

10. The system of claim 1, wherein said one or more heater balls comprise a plurality of said heater elements, which said heater elements are independently controllable by said processing unit.

11. The system of claim 1, wherein each said heater ball contains a programmable memory for storing information, such that a group of heater balls may be programmed with a common identification number so that said group of heater balls may be addressed and controlled cooperatively by said processing unit.

12. A method of treating tumors, comprising:
providing a processing unit equipped with an antenna for transmitting and receiving signals, and including input control means and display means; and
disposing one or more miniature substantially spherical heater balls proximate to the tumor, each heater ball including one or more heater elements and integrated circuitry for controlling the heater elements to radiate heat to the tumor, the integrated circuitry including input/output data communication circuitry and signal processing circuitry for communicating with the processing unit.

13. The method of claim 12, further comprising the step of injecting with a catheter delivery system one or more heater balls into the tumor.

14. The method of claim 13, wherein the step of injecting delivers the heater balls to the tumor in a viscous slurry using the catheter delivery system.

15. The method of claim 12, wherein the heater balls each include a unique identification number, and the processing unit can uniquely address and separately control each heater ball.

16. The method of claim 12, wherein the one or more heater balls further comprise a temperature sensor and further comprising the step of sensing a temperature parameter of the one or more heater elements and transmitting sensed temperature information to the processing unit.

17. The method of claim 16, further comprising an analog-to-digital converter on each heater ball for converting the temperature parameter to digital data.

* * * * *